United States Patent [19]

Tice

[11] Patent Number: 5,300,477
[45] Date of Patent: Apr. 5, 1994

[54] 2-ARYLPYRIMIDINES AND HERBICIDAL USE THEREOF

[75] Inventor: Colin M. Tice, Melrose Park, Pa.

[73] Assignee: Rohm and Haas Company, Philadelphia, Pa.

[21] Appl. No.: 62,802

[22] Filed: May 20, 1993

Related U.S. Application Data

[63] Continuation-in-part of Ser. No. 916,247, Jul. 17, 1992, abandoned.

[51] Int. Cl.$^5$ ............... C07D 239/36; C07D 401/04; A01N 43/54
[52] U.S. Cl. ............................ 504/242; 504/243; 504/193; 544/229; 544/319
[58] Field of Search ............... 544/319, 229; 504/193, 504/242, 243

[56] References Cited

U.S. PATENT DOCUMENTS

| | | | |
|---|---|---|---|
| 4,431,440 | 2/1984 | Bhalla et al. | 544/289 |
| 4,771,040 | 9/1988 | Maurer et al. | 544/243 |
| 4,908,379 | 3/1990 | Nakajima et al. | 544/299 |

FOREIGN PATENT DOCUMENTS

| | | |
|---|---|---|
| 339105 | 11/1989 | European Pat. Off. |
| 243496 | 3/1987 | Fed. Rep. of Germany |

OTHER PUBLICATIONS

Kronberg, L. et al. Acta. Pharm. Suecica, pp. 37–46, 1970.
Bogentoft et al. Acta Pharm. Suecica, pp. 489–500, 1969.
Staskun, B. et al. J. Chem. Soc, 4708–4710, 1956.
Hirokami, S. et al. J. Organ Chem., 2455–2468, 1987.
Sitte et al. Chem. Ber. vol. 102, pp. 615–622 (1969).
Mussetta, M. T. et al. C. R. Acad. Sci. Ser. C, 1341–1344, 1973.
Harris, R. L. N. et al. Angew. Chem. Int. Ed (Engl). pp. 779–780, 1977.
Nishio, T. et al. J. Chem. Soc. Perkin, pp. 2523–2529, 1987.
Oostveen, E. A. et al. Recl. Trav. Chim. Pays-Bas, pp. 68–72, 1977.
Culbertson, T. B. J. Heterocycl. Chem., pp. 1423–1424, 1979.
Botta, M. et al. Arch Pharm. (Weinheim), pp. 203–207, 1991.
Briel, D. et al. Arch Pharm. (Weinheim), pp. 1145–1147, 1985.
Juby, P. F. et al. J. Med. Chem., pp. 263–269, 1979.
Gupta, K. A. et al. Synthesis, pp. 905–907, 1981.
J. Org. Chem, vol. 58, No. 16, pp. 4490–4493, 1993 Veale et al.

Primary Examiner—John M. Ford
Attorney, Agent, or Firm—Clark R. Carpenter

[57] ABSTRACT

A class of 2-arylpyrimidines which is useful in the control of weeds is of the general formula:

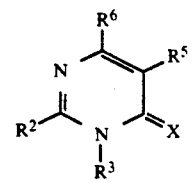

wherein $R^2$ is an optionally substituted aromatic ring; $R^3$ is a saturated or unsaturated alkyl group; $R^5$ is selected from hydrogen, halo, alkyl, alkenyl, alkynyl, alkoxy, and alkylthio; $R^6$ is selected from hydrogen, halo, alkyl, haloalkyl, aryl, and alkoxy; and X is oxygen or sulfur.

13 Claims, No Drawings

2-ARYLPYRIMIDINES AND HERBICIDAL USE THEREOF

This application is a continuation-in-part of application Ser. No. 07/916,247, filed Jul. 17, 1992, now abandoned.

BACKGROUND OF THE INVENTION

A need continues for novel and improved herbicidal compounds and compositions. This is particularly so since the targets of herbicides can become resistant to known herbicides over time and after use of such compositions. Additionally, economic and environmental considerations can favor herbicides having different modes of performance than those currently used. This invention relates to novel arylpyrimidines and their use as broad spectrum herbicides.

SUMMARY OF THE INVENTION

2-Arylpyrimidines which are useful in the control of weeds have been discovered. These compounds are of the general formula:

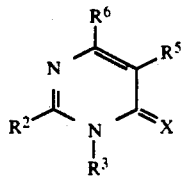

wherein $R^2$ is a substituted or unsubstituted aryl or heteroaromatic group; $R^3$ is an alkyl, haloalkyl, polyhaloalkyl, alkenyl, haloalkenyl, polyhaloalkenyl, alkynyl, haloalkynyl, polyhaloalkynyl, alkenynyl, alkoxyalkyl, dialkoxyalkyl, haloalkoxyalkyl, oxoalkyl, trimethylsilylalkynyl, cyanoalkyl or aryl group; $R^5$ is a hydrogen, halo, alkyl, alkenyl, alkynyl, alkoxy, alkylthio, alkoxycarbonylalkyl, haloalkyl, haloalkenyl, haloalkynyl, haloalkoxy, polyhaloalkyl, polyhaloalkenyl, polyhaloalkynyl, polyhaloalkoxy, trimethylsilylalkynyl, or cyano group; and $R^6$ is a hydrogen, halo, alkyl, alkenyl, alkynyl, alkoxy, alkylthio, haloalkylthio, alkoxyalkyl, alkoxycarbonyl, alkoxycarbonylalkyl, haloalkyl, haloalkoxy, haloalkenyl, haloalkynyl, polyhaloalkyl, polyhaloalkoxy, polyhaloalkylthio, polyhaloalkenyl, polyhaloalkynyl, cycloalkyl, aryl, aryloxy, heterocyclyl, aralkyl, alkylamino, dialkylamino, dialkylaminocarbonyl, or cyano group; and X is oxygen or sulfur. It is to be understood that the prefix term "halo" designates a halogen substituent (such as fluorine, chlorine, bromine, or iodine) and that "polyhalo" designates two or more substituents independently selected halogens. It is further to be understood that, unless otherwise specified, use of the prefix "halo" without a concurrent use of the prefix "polyhalo" is not intended to limit the invention to singularly halogenated compounds. This invention also teaches methods of preparing these compounds as well as methods of using the compounds as herbicides.

EMBODIMENTS OF THE INVENTION

Embodiments of the present invention are described in the following compound embodiments, methods of preparation, methods of use and compositions (formulations). While the invention is exemplified in these descriptions, such are not intended to limit the scope of the invention.

COMPOUND EMBODIMENTS.

An embodiment of the present invention are compounds of the general formula:

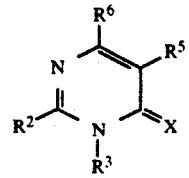

wherein $R^2$ is a substituted or unsubstituted aryl group (e.g. aromatic ring structure having six to ten carbon atoms) or a substituted or unsubstituted heteroaromatic group (e.g. a heteroaromatic ring structure having four to five carbon atoms and one heteroatom selected from the group consisting of nitrogen, sulfur and oxygen); $R^3$ is an alkyl, haloalkyl, polyhaloalkyl, haloalkenyl, polyhaloalkenyl, alkenyl, alkynyl, haloalkynyl, polyhaloalkynyl, alkenynyl, alkoxyalkyl, dialkoxyalkyl, haloalkoxyalkyl, oxoalkyl, trimethylsilylalkynyl, cyanoalkyl or aryl group; $R^5$ is a hydrogen, halo, alkyl, alkenyl, alkynyl, alkoxy, alkylthio, alkoxycarbonylalkyl, haloalkyl, haloalkenyl, haloalkynyl, haloalkoxy, polyhaloalkyl, polyhaloalkenyl, polyhaloalkynyl, polyhaloalkoxy, trimethylsilylalkynyl, or cyano group; and $R^6$ is a hydrogen, halo, alkyl, alkenyl, alkynyl, alkoxy, alkylthio, alkoxyalkyl, alkoxycarbonyl, alkoxycarbonylalkyl, haloalkyl, haloalkenyl, haloalkynyl, haloalkoxy, haloalkylthio, polyhaloalkyl, polyhaloalkenyl, polyhaloalkynyl, polyhaloalkoxy, polyhaloalkylthio, cycloalkyl, aryl, aryloxy, heterocyclyl, aralkyl, alkylamino, dialkylamino, dialkylaminocarbonyl, or cyano group; and X is oxygen or sulfur.

$R^2$ is an aryl or heteroaromatic group, preferably furyl, phenyl, naphthyl, pyridyl, or thienyl, and may be optionally substituted with up to three substituents independently selected from bromo; chloro; fluoro; $(C_1-C_{12})$alkyl, preferably $(C_1-C_6)$alkyl; cyclo$(C_3-C_8)$alkyl, preferably cyclo$(C_5-C_6)$alkyl; $(C_2-C_{12})$alkenyl, preferably $(C_2-C_6)$alkenyl; cyclo$(C_3-C_8)$alkenyl; $(C_2-C_{12})$alkynyl, preferably $(C_2-C_6)$alkynyl; halo$(C_1-C_{12})$alkyl, preferably halo$(C_1-C_6)$alkyl; polyhalo$(C_1-C_{12})$alkyl, preferably polyhalo$(C_1-C_6)$alkyl; halo$(C_2-C_{12})$alkenyl, preferably halo$(C_2-C_6)$alkenyl; polyhalo$(C_2-C_{12})$alkenyl, preferably polyhalo$(C_2-C_6)$alkenyl; halo$(C_2-C_6)$alkynyl; polyhalo$(C_2-C_6)$alkynyl; $(C_1-C_{12})$alkoxy, preferably $(C_1-C_6)$alkoxy; $(C_1-C_{12})$alkylthio, preferably $(C_1-C_6)$alkylthio; $(C_1-C_{12})$alkylsulfonyl; $(C_1-C_{12})$alkylsulfinyl; phenyl; phen$(C_1-C_{12})$alkyl; phen$(C_2-C_{12})$alkenyl; phen$(C_2-C_{12})$alkynyl; cyano; halo$(C_1-C_{12})$alkoxy, preferably halo$(C_1-C_6)$alkoxy; 1,3-dioxalan-2-yl; hydroxyimino, polyhalo$(C_1-C_{12})$alkoxy, ; and nitro. Substituent groups can be branched or unbranched. Preferred phenyl groups are phenyl, 3-methylphenyl, 3-methoxyphenyl, 3-nitrophenyl, 4-fluorophenyl, 4-chlorophenyl, 3-trifluoromethylphenyl, 3-bromophenyl, 3-chlorophenyl, 3-fluorophenyl, 3-trifluoromethoxyphenyl, 3-cyanophenyl, 3-(1,3-dioxalan-2-yl)phenyl, 3-(hydroxyimino)phenyl, 2-fluorophenyl, 2-chlorophenyl, 2-trifluoromethoxyphenyl, 3,5-difluorophenyl, 3,5-dichlorophenyl, 2,4-difluorophenyl, 2,5-difluorophenyl, 3-chloro-4-fluorophenyl, 3,4- difluorophenyl, 3-fluoro-5-trifluoromethylphenyl, 3,4,5-trifluorophenyl; more preferably phenyl, 3-fluorophenyl, and 3-chlorophenyl. Preferred pyridyl groups are 6-chloro-2-pyridyl; 3-pyridyl; 1-methyl-3-pyridinium; 5-bromo-3-pyridyl; 5,6-dichloro-3-pyridyl; 5-chloro-3-pyridyl, 1-oxo-3-pyridyl; 4-pyridyl; 2-fluoro-4-pyridyl; 2-chloro-4-pyridyl; 2-chloro-6-methyl-4-pyridyl; 2-methyl-4-pyridyl, 2-methoxy-4-pyridyl, 2-cyano-4-pyridyl,1-oxo-4-pyridyl, 2,6-difluoro-4-pyridyl and 2,6-dichloro-4-pyridyl. More preferred are 2-chloro-4-pyridyl; 2-fluoro-4-pyridyl; and 2,6-dichloro-4-pyridyl. The pyridyl groups can also be present as a salt, such as 1-methyl-3-pyridinium iodide or 3-pyridinium hydrochloride. Preferred furyl groups are 2-furyl and 3-furyl. A preferred naphthyl group is 2-naphthyl. Preferred thienyl groups are 2-thienyl, 3-thienyl, 4-chloro-2-thienyl, 5-chloro-2-thienyl, 5-chloro-3-thienyl and 2,5-dichloro-3-thienyl.

In the case of $R^2$ being a pyridyl group, an additional selection of substituent groups is oxygen substituted on the nitrogen atom of the pyridyl ring; e.g. N-oxo groups, such as 1-oxo-3-pyridyl or 1-oxo-4-pyridyl. Optionally, each of the furyl, phenyl, naphthyl, pyridyl and thienyl groups can have a fused ring moiety such that the fused ring is composed of alkylenedioxy, e.g. an oxymethyleneoxy (—O—$CH_2$—O—) link or an oxyethyleneoxy (—O—$CH_2CH_2$—O—) link which is bonded to adjacent carbon atoms of the group. For example, 3,4-methylenedioxyphenyl.

$R^3$ is an alkyl, alkenyl, alkynyl, alkenynyl, alkoxyalkyl, dialkoxyalkyl, haloalkoxyalkyl, oxoalkyl, trimethylsilylalkynyl, cyanoalkyl or aryl group. Preferably, $R^3$ is a ($C_1$–$C_3$)alkyl; ($C_3$–$C_4$)alkenyl; or ($C_3$–$C_6$)alkynyl group, each of which may be optionally substituted with up to five halogens; or a ($C_1$–$C_6$)alkoxy($C_1$–$C_6$)alkyl, di($C_1$–$C_6$)alkoxy($C_1$–$C_6$)alkyl, halo($C_1$–$C_6$)alkoxy($C_1$–$C_6$)alkyl, 2-oxo($C_2$–$C_3$)alkyl trimethylsilyl($C_3$–$C_4$)alkynyl or cyano($C_1$–$C_6$)alkyl group. A preferred ($C_1$–$C_3$)alkyl group is ethyl. Preferred alkenyl and halogen substituted alkenyl groups are ($C_3$–$C_4$)alkenyls, such as allyl and 3-chloroallyl. Preferred alkynyl groups are ($C_3$–$C_6$)alkynyl, such as pentynyl, propynyl and butynyl, more preferably pent-2-ynyl, prop-2-ynyl, and but-2-ynyl. Preferred halogen substituted ($C_3$–$C_6$)alkynyl groups are iodopropargyl and bromopropargyl. Preferred ($C_1$–$C_6$)alkoxy($C_1$–$C_6$)alkyls are ($C_1$–$C_2$)alkoxy($C_1$–$C_3$)alkyl, more preferably methoxymethyl and 2-methoxyethyl, and most preferably methoxymethyl. Preferred di($C_1$–$C_6$)alkoxy($C_1$–$C_6$)alkyls are di($C_1$–$C_2$)alkoxy($C_1$–$C_3$)alkyls, more preferably 2,2-dimethoxypropyl. A preferred 2-oxo($C_2$–$C_3$)alkyl is acetonyl. A preferred trimethylsilyl ($C_3$–$C_4$)alkynyl is 3-(trimethylsilyl)propargyl. A preferred cyano ($C_1$–$C_6$)alkyl is cyanomethyl. Preferred alkenynyls are ($C_5$–$C_6$)alkenynyls, more preferably pent-4-en-2-ynyl.

$R^5$ is a hydrogen, halo, alkyl, alkenyl, alkynyl, alkoxy, alkylthio, alkoxycarbonylalkyl, haloalkyl, haloalkenyl, haloalkynyl, haloalkoxy, polyhaloalkyl, polyhaloalkenyl, polyhaloalkynyl, polyhaloalkoxy, trimethylsilylalkynyl or cyano group. Preferred $R^5$ substituents are hydrogen, ($C_1$–$C_5$)alkyl, ($C_3$–$C_6$)alkenyl, ($C_2$–$C_6$)alkynyl, trimethylsilyl($C_2$–$C_3$)alkynyl, ($C_1$–$C_6$)alkoxy, halo- or polyhalo($C_1$–$C_6$)alkyl, halo- or polyhalo($C_2$–$C_6$)alkenyl, halo- or polyhalo($C_2$–$C_6$)alkynyl, halo ($C_1$–$C_6$)alkoxy, polyhalo ($C_1$–$C_6$)alkoxy, ($C_1$–$C_3$)alkoxycarbonyl($C_1$–$C_3$)alkyl, ($C_1$–$C_6$)alkylthio, halo and cyano. Preferred ($C_1$–$C_5$)alkyls are methyl, ethyl, n-propyl and iso-propyl, more preferably methyl and ethyl.

Preferred ($C_2$–$C_6$)alkynyls are ($C_2$–$C_4$)alkynyls, more preferably prop-2-ynyl. Preferred ($C_1$–$C_6$)alkoxys are ($C_1$–$C_2$)alkoxys, more preferably methoxy. Preferred ($C_1$–$C_6$)alkylthios are ($C_1$–$C_2$)alkylthios, more preferably methylthio. A preferred alkoxycarbonyalkyl is methoxycarbonylmethyl. Preferred ($C_3$–$C_6$)alkenyls are ($C_3$–$C_4$)alkenyl, more preferably allyl. Preferred halo($C_1$–$C_6$)alkyls and polyhalo($C_1$–$C_6$)alkyls are halo($C_1$–$C_2$)alkyls and polyhalo($C_1$–$C_2$)alkyls, more preferably fluoromethyl and trifluoromethyl. Preferred halo($C_1$–$C_6$)alkoxys and polyhalo($C_1$–$C_6$)alkoxys are halo($C_1$–$C_2$)alkoxys, and polyhalo($C_1$–$C_2$)alkoxys more preferably difluoromethoxy and trifluoromethoxy. Preferred halos are chloro and fluoro. A preferred trimethylsilyl($C_2$–$C_3$)alkynyl is trimethylsilylethynyl.

$R^6$ is a hydrogen, halo, alkyl, alkenyl, alkynyl, alkoxy, alkylthio, alkoxyalkyl, alkoxycarbonyl, alkoxycarbonylalkyl, haloalkyl, polyhaloalkyl, cycloalkyl, haloalkylthio, haloalkenyl, polyhaloalkenyl, haloalkynyl, polyhaloalkynyl, haloalkoxy, polyhaloalkoxy, polyhaloalkylthio, aryl, aryloxy, heterocyclyl selected from furyl, pyridyl and thienyl, aralkyl, alkylamino, dialkylamino, dialkylaminocarbonyl, or cyano group. Preferred $R^6$ are hydrogen, halo, straight ($C_1$–$C_8$)alkyl, branched ($C_3$–$C_8$)alkyl, ($C_2$–$C_6$)alkenyl, ($C_2$–$C_6$)alkynyl, halo($C_1$–$C_6$)alkyl or polyhalo($C_1$–$C_6$)alkyl, halo($C_2$–$C_6$)alkenyl or polyhalo($C_2$–$C_6$)alkenyl, halo($C_2$–$C_6$)alkynyl or polyhalo($C_2$–$C_6$)alkynyl, ($C_1$–$C_6$)alkoxy($C_1$–$C_4$)alkyl, ($C_1$–$C_6$)alkoxy, ($C_1$–$C_6$)alkylthio, ($C_1$–$C_3$)alkoxycarbonyl, ($C_1$–$C_3$)alkoxycarbonyl($C_1$–$C_3$)alkyl, substituted or unsubstitued ($C_6$–$C_{10}$)aryl, substituted or unsubstituted ($C_6$–$C_{10}$)aryloxys, substituted or unsubstituted ar($C_1$–$C_4$)alkyl, cyclo($C_3$–$C_7$)alkyl, halo($C_1$–$C_6$)alkylthio, polyhalo ($C_1$–$C_6$)alkythio, halo($C_1$–$C_6$)alkoxy, polyhalo ($C_1$–$C_6$)alkoxy, ($C_4$–$C_5$)heterocyclyl, ($C_1$–$C_3$)alkylamino, di($C_1$–$C_3$)alkylamino, di($C_1$–$C_3$)alkylaminocarbonyl, and cyano. The aryl portion of the foregoing ($C_6$–$C_{10}$)aryl, ($C_6$–$C_{10}$)aryloxy and aryl($C_1$–$C_4$)alkyl groups can be optionally substituted with up to three substituents independently selected from bromo; chloro; fluoro; ($C_1$–$C_{12}$)alkyl, preferably ($C_1$–$C_6$)alkyl; cyclo($C_3$–$C_8$)alkyl, preferably cyclo($C_5$–$C_6$)alkyl; ($C_2$–$C_{12}$)alkenyl, preferably ($C_2$–$C_6$)alkenyl; cyclo($C_3$–$C_8$)alkenyl; ($C_2$–$C_{12}$)alkynyl, preferably ($C_2$–$C_6$)alkynyl; halo($C_1$–$C_{12}$)alkyl, preferably halo($C_1$–$C_6$)alkyl; polyhalo($C_1$–$C_{12}$)alkyl, preferably polyhalo($C_1$–$C_6$)alkyl; halo($C_2$–$C_{12}$)alkenyl, preferably halo($C_2$–$C_6$)alkenyl; polyhalo($C_2$–$C_{12}$)alkenyl, preferably polyhalo($C_2$–$C_6$)alkenyl; halo($C_2$–$C_6$)alkynyl; polyhalo($C_2$–$C_6$)alkynyl; ($C_1$–$C_{12}$)alkoxy, preferably ($C_1$–$C_6$)alkoxy; ($C_1$–$C_{12}$)alkylthio, preferably ($C_1$–$C_6$)alkylthio; ($C_1$–$C_{12}$)alkylsulfonyl; ($C_1$–$C_{12}$)alkylsulfinyl; phenyl; phen($C_1$–$C_{12}$)alkyl; phen($C_2$–$C_{12}$)alkenyl; phen($C_2$–$C_{12}$)alkynyl; cyano; halo($C_1$–$C_{12}$)alkoxy, preferably halo($C_1$–$C_6$)alkoxy; 1,3-dioxalan-2-yl; hydroxyimino; and nitro. Preferred ($C_1$–$C_8$)alkyls are straight ($C_1$–$C_7$)alkyls and branched ($C_3$–$C_8$)alkyls, preferably methyl, ethyl, n-propyl, n-butyl, n-pentyl, n-hexyl, n-heptyl, s-butyl, i-propyl, i-butyl and t-butyl; more preferably methyl, ethyl, n-propyl, s-butyl, i-propyl and t-butyl. A preferred ($C_2$–$C_6$)alkenyl is 2-methyl-1-propenyl. A preferred ($C_6$–$C_{10}$)aryl is phenyl. A preferred ($C_6$–$C_{10}$)aryloxy is phenoxy. Preferred ($C_4$–$C_5$)heterocyclyls are 3-thienyl, 3-furyl, 2-thienyl and 4-pyridyl; most preferably 3-thienyl. Preferred ($C_1$–$C_6$)alkoxys are ($C_1$–$C_5$)alkoxys, more preferably methoxy and ethoxy. A preferred ($C_1$–$C_3$)alkoxycarbonyl is ethoxycarbonyl. Preferred ($C_2$–$C_6$)alkynyls are but-2-ynyl, but-3-ynyl, and prop-2-ynyl. Preferred halos are fluoro, bromo, and chloro; more preferably chloro and bromo. Preferred halo($C_1$–$C_6$)alkyls and polyhalo($C_1$–$C_6$)alkyls are halo($C_1$–$C_3$)alkyls and polyhalo($C_1$–$C_3$)alkyls, more preferably trifluoromethyl, pentafluoroethyl, trichloromethyl, bromomethyl, chloromethyl, difluoromethyl, and chlorodifluoromethyl; most preferably trifluoromethyl. Preferred halo($C_1$–$C_6$)alkoxys and polyhalo($C_1$–$C_6$)alkoxys are halo($C_1$–$C_3$)alkoxys and polyhalo($C_1$–$C_3$)alkoxys, more preferably difluoromethoxy and trifluoromethoxy. Preferred ($C_1$–$C_6$)alkylthios are ($C_1$–$C_5$)alkylthios, more preferably methylthio. A preferred ($C_1$–$C_6$)alkoxy($C_1$–$C_4$)alkyl is methoxymethyl. A preferred ar($C_1$–$C_4$)alkyl is benzyl. Preferred cyclo($C_3$–$C_7$)alkyls are cyclopropyl, cyclobutyl and cyclopentyl. A preferred di($C_1$–$C_3$)alkylamino is dimethylamino. A preferred di($C_1$–$C_3$)alkylaminocarbonyl is dimethylaminocarbonyl.

X is oxygen or sulfur, preferably oxygen.

A preferred embodiment of this invention are the compounds represented by formula I wherein X is oxygen and $R^2$ is substituted or unsubstituted phenyl, pyridyl, or thienyl.

A more preferred embodiment of this invention are the compounds represented by formula I wherein X is oxygen; $R^2$ is substituted or unsubstituted phenyl, substituted or unsubstituted pyridyl or substituted or unsubstituted thienyl; and $R^3$ is ($C_3$–$C_6$)alkynyl.

A still more preferred embodiment of this invention is the compound represented by formula I wherein X is oxygen; $R^2$ is substituted or unsubstituted phenyl, substituted or unsubstituted pyridyl or substituted or unsubstituted thienyl; $R^3$ is ($C_3$–$C_6$)alkynyl; and $R^5$ and $R^6$ are independently selected from hydrogen, halo, ($C_1$–$C_4$)alkyl, polyhalo($C_1$–$C_4$)alkyl, and ($C_1$–$C_4$)alkoxy. $R^6$ can be also unsubstituted or substituted phenyl.

Even more preferred is the compound represented by formula I wherein X is oxygen; $R^2$ is phenyl, 3-substituted phenyl (i.e. meta-substituted phenyl), 3,5-disubstituted-phenyl or 3,4,5-trisubstituted phenyl, 2-substituted-4-pyridyl or 2,6-disubstituted-4-pyridyl or 3-thienyl or 5-substituted-3-thienyl; $R^3$ is ($C_3$–$C_6$)alkynyl; and $R^5$ and $R^6$ are independently selected from hydrogen, halo, ($C_1$–$C_4$)alkyl, polyhalo($C_1$–$C_4$)alkyl and ($C_1$–$C_4$)alkoxy. $R^6$ can be also unsubstituted or substituted phenyl.

A yet more preferred embodiment of this invention is the compound represented by formula I wherein X is oxygen; $R^2$ is phenyl, 3-fluorophenyl, 3-chlorophenyl, 3,5-difluorophenyl, 3,5-dichlorophenyl, 3,4,5-trifluorophenyl, 2-chloro-4-pyridyl, 2-fluoro-4-pyridyl, 2,6-dichloro-4-pyridyl or 3-thienyl or 5-chloro-3-thienyl; $R^3$ is propargyl; $R^5$ is hydrogen, methyl, ethyl, methoxy, fluoro or chloro; and $R^6$ is methyl, ethyl, isopropyl, n-propyl, n-butyl, s-butyl, i-butyl, t-butyl, trifluoromethyl, difluoromethyl, phenyl, chloro, bromo, or fluoro.

Preferred compounds are
(a) 5,6-diethyl-2-phenyl-3-propargyl-4(3H)-pyrimidinone;
(b) 5-ethyl-2-phenyl-3-propargyl-6-trifluoromethyl-4(3H)-pyrimidinone;
(c) 5-ethyl-6-(1-methylethyl)-2-phenyl-3-propargyl-4(3H)-pyrimidinone;
(d) 6-chloro-5-ethyl-2-phenyl-3-propargyl-4(3H)-pyrimidinone;
(e) 5,6-diethyl-2-(3-fluorophenyl)-3-propargyl-4(3H)-pyrimidinone;
(f) 2-(2,6-dichloro-4-pyridyl)-5,6-diethyl-3-propargyl-4(3H)-pyrimidinone;
(g) 5,6-diethyl-2-(3,5-difluorophenyl)-3-propargyl-4(3H)-pyrimidinone;
(h) 5-ethyl-2-phenyl-3-propargyl-6-propyl-4(3H)-pyrimidinone;
(i) 6-difluoromethyl-5-ethyl-2-phenyl-3-propargyl-4(3H)-pyrimidinone; or
(j) 6-ethyl-5-methoxy-2-phenyl-3-propargyl-4(3H)-pyrimidinone.

Compounds encompassed by the present invention include, but are not limited to, those illustrated in Table 1. The synthesis methods (i.e., "A", "B" etc.) specified in the table are described hereinafter in this specification. The sequence of letters in the "Synthesis" column indicated the relative sequence of steps performed. For instance, "D+A" indicates the steps of procedure D were first performed, followed by the steps of Procedure A.

TABLE 1

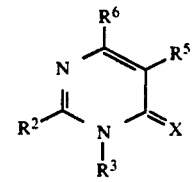

For the below table, "Me" is methyl, "Et" is ethyl, "Pr" is propyl, "Bu" is butyl, "Pe" is pentyl, "Bn" is benzyl, and "Ph" is phenyl; and except as noted, X=O (oxygen).

| Compound No. | $R^2$ | $R^3$ | $R^5$ | $R^6$ | MP °C. | Synthesis |
|---|---|---|---|---|---|---|
| 1 | —Ph | —CH$_2$C≡CH | —Me | —Me | 125–128 | D + A |
| 2 | —Ph | —CH$_2$C≡CH | —H | —Me | 148–149 | D + A |
| 4 | —Ph | —CH$_2$C≡CH | —H | —CF$_3$ | 118–120 | D + A |
| 5 | —Ph | —CH$_2$C≡CH | —Me | —Et | 115–117 | D + A |
| 6 | —Ph | —CH$_2$OCH$_3$ | —H | —CF$_3$ | 89–90 | D + Z6 |
| 7 | —Ph | —CH$_2$C≡CH | —Br | —CF$_3$ | 156–160 | D + Y1 + A |
| 8 | —Ph | —CH$_2$C≡CH | —Me | —Ph | 170–173 | D + A |
| 9 | —Ph | —CH$_2$C≡CH | —Cl | —Me | 131–134 | D + A |
| 11 | —Ph | —CH$_2$C≡CH | —H | -t-C$_4$H$_9$ | Oil | D + A |
| 12 | —Ph | —CH$_2$C≡CH | —H | —Pr | 72.5–74 | D + A |
| 13 | —Ph | —CH$_2$C≡CH | -i-Pr | —Me | 79–80.5 | D + A |
| 14 | —Ph | —CH$_2$C≡CH | —Et | —Me | 103–106 | D + A |
| 15 | —Ph | —Et | —Me | —Me | 77–78 | D + A |
| 16 | —Ph | —CH$_2$C≡CH | —Me | —Cl | 137.5–139 | E + H + I + A |
| 17 | —Ph | —CH$_2$C≡CH | -n-Pe | —Me | 92–93.5 | D + A |

-continued

| Compound No. | R² | R³ | R⁵ | R⁶ | MP °C. | Synthesis |
|---|---|---|---|---|---|---|
| 18 | —Ph | —CH₂CH=CH₂ | —H | —CF₃ | Oil | D + A |
| 19 | —Ph | —CH₂C≡CH | —Me | —C(O)NMe₂ | 137–140 | D + A + Z1 |
| 20 | —Ph | —Et | —H | —CF₃ | Solid | B |
| 21 | —Ph | —CH₂C≡CCH₂CH₃ | —H | —CF₃ | 99–100.5 | D + A |
| 22 | —Ph | —CH₂C≡CH | —Et | —Et | 101–103 | D + A |
| 23 | —Ph | —CH₂C≡CH | —Me | —NMe₂ | 111.5–113.5 | E + H + I + A + Z2 |
| 25 | —Ph | —CH₂C(O)Me | —Me | —C₂H₅ | 87–89 | D + Z3 |
| 26 | —Ph | —CH₂C≡CH | —Me | —SMe | 156–159 | E + H + I + A + Z4 |
| 27 | —Ph | —CH₂C≡CH | —H | —C₂F₅ | 134–136 | D + A |
| 28 | —Ph | —CH₂C≡CH | —Et | —Ph | 124–126 | D + A |
| 29 | —Ph | —CH₂C≡CH | —Me | —CF₃ | 143–145 | D + A |
| 30 | —Ph | —CH₂C≡CH | -n-Pr | —CF₃ | 155–157 | D + A |
| 31 | —Ph | —CH₂C≡CH | —OMe | —CF₃ | 103–106 | D + A |
| 32 | —Ph | —CH₂C≡CH | —H | —C₂H₅ | 101–103 | D + A |
| 33 | —Ph | —CH₂C≡CH | —Me | —CH₂OMe | 125–127 | D + A |
| 35 | -4-ClPh | —CH₂C≡CH | —Me | —Et | 109–111 | D + A |
| 36 | —Ph | —CH₂C(OMe)₂Me | —Me | —Et | 85–88 | D + A + Z5 |
| 37 | —Ph | —CH₂CH₂OMe | —H | —CF₃ | 49–51 | B |
| 38 | —Ph | —CH₂C≡CH | —CN | —SMe | 189–191 | A |
| 39 | —Ph | —CH₂C≡CCH₃ | —H | —CF₃ | 85–88 | D + A |
| 40 | —Ph | —CH₂C≡CH | —F | —Cl | 113–115 | D + H + I + A |
| 41 | —Ph | —Ph | —H | —CF₃ | 149–151 | B |
| 45 | —Ph | —CH₂C≡CH | —H | —CCl₃ | 86–91 | D + A |
| 46 | —Ph | —CH₂C≡CH | —Et | —CF₃ | 113–115 | B or D + A |
| 47 | —Ph | —CH₂C≡CH | —SMe | —CF₃ | 159–162 | D + A |
| 48 | —Ph | —CH₂C≡CH | —Me | i-Pr | 120–122 | D + A |
| 51 | —Ph | —CH₂C≡CH | —Me | —H | 135–136 | D + A |
| 52 | —Ph | —CH₂C≡CH | —Me | —CO₂Et | 147–150 | D + A |
| 53 | —Ph | —CH₂CH=CH₂ | —Et | —CF₃ | 73–76 | B |
| 54 | -2-Cl-4-pyridyl | —CH₂C≡CH | —Et | —CF₃ | 82–84 | B |
| 55 | —Ph | —CH₂C≡CH | —Et | -n-Bu | 57–59 | D + A |
| 56 | -2-Cl-4-pyridyl | —CH₂C≡CH | —Et | —Et | 84–86 | D + A |
| 57 | -3,5-diClPh | —CH₂C≡CH | —Et | —Et | 113–114 | D + A |
| 58 | -4-pyridyl | —CH₂C≡CH | —Et | —CF₃ | 114–116 | B |
| 59 | -2-Cl-6-Me-4-pyridyl | —CH₂C≡CH | —Et | —Et | 119–121 | D + A |
| 60 | -3-pyridyl | —CH₂C≡CH | —Et | —CF₃ | 116–118 | B |
| 61 | -1-Me-3-pyridinium iodide | —CH₂C≡CH | —Et | —CF₃ | >170 (dec) | B + Z13 |
| 62 | -2-F-4-pyridyl | —CH₂C≡CH | —Et | —CF₃ | Oil | B |
| 63 | -5,6-diCl-3-pyridyl | —CH₂C≡CH | —Et | —CF₃ | 89–92 | B |
| 64 | -3,4-diFPh | —CH₂C≡CH | —Et | —Et | 97–99 | D + A |
| 65 | -2,6-diCl-4-pyridyl | —CH₂C≡CH | —Et | —CF₃ | 129–131 | B |
| 66 | -5-Br-3-pyridyl | —CH₂C≡CH | —Et | —CF₃ | 123–125 | B |
| 67 | -2,6-diCl-4-pyridyl | —CH₂C≡CH | —Et | i-Pr | solid | D + A |
| 68 | -4-FPh | —CH₂C≡CH | —Et | —Et | 107–109 | D + A |
| 69 | -3-formylPh | —CH₂C≡CH | —Et | —Et | 82–86 | D + A + Z14 |
| 70 | -2,4-diFPh | —CH₂C≡CH | —Et | —Et | 68–71 | D + A |
| 71 | -2,5-diFPh | —CH₂C≡CH | —Et | —Et | 99–102 | D + A |
| 76 | —Ph | —CH₂C≡CH | —Cl | —CF₃ | 135–138 | D + A |
| 77 | -3-ClPh | —CH₂C≡CH | —H | —CF₃ | 103–106 | D + A |
| 79 | —Ph | —Me | —SMe | —CF₃ | 110–112 | D + A |
| 80 | -2-thienyl | —CH₂C≡CH | —H | —Me | 103.5–105 | A |
| 81* | —Ph | —CH₂C≡CH | —H | —CH₂Cl/—CH₂Br mixture | solid | A |
| 83 | -3-thienyl | —CH₂C≡CH | —H | —Et | 97–99 | A |
| 84 | —Ph | —CH₂C≡CH | —CH₂C≡CH | —Et | 128–130 | D + A |
| 86 | —Ph | —CH₂C≡CH | —Et | -i-Pr | 92–94 | D + A |
| 87 | -3-NO₂—Ph | —CH₂C≡CH | —Et | —Et | 114–119 | D + A |
| 88 | -3-CF₃—Ph | —CH₂C≡CH | —Et | —Et | 67–70 | D + A |
| 89 | —Ph | —CH₂C≡CH | —Br | —Ph | 166–169 | D + Y1 + A |
| 90 | -3-FPh | —CH₂C≡CH | —Et | —Et | 114–116 | D + A |
| 91 | —Ph | —CH₂C≡CH | —I | —Et | 175–177 | D + Y2 + A |
| 92 | —Ph | —CH₂C≡CH | —C≡CSiMe₃ | —Et | Oil | D + Y2 + A + Z7 |
| 94 | -2-FPh | —CH₂C≡CH | —Et | —Et | 76.5–79 | D + A |
| 95 | -3-MePh | —CH₂C≡CH | —Et | —Et | 70–73 | D + A |
| 96 | -3-MeO—Ph | —CH₂C≡CH | —Et | —Et | 72–75 | D + A |
| 97 | —Ph | —CH₂C≡CH | —Et | —Br | 94–95 | E + H + I + A |
| 98 | -3-ClPh | —CH₂C≡CH | —Et | —Et | 109–111.5 | D + A |
| 99 | -3-thienyl | —CH₂C≡CH | —Et | —Et | 123–126.5 | D + A |
| 103 | —Ph | —CH₂C≡CH | —Et | -n-Pr | 82.5–85 | D + A |
| 105 | —Ph | —CH₂C≡CH | CH₂CO₂Me | —Et | 153–154 | D + A |
| 106 | —Ph | —CH₂C≡CH | —Et | —Cl | 108–109.5 | E + H + I + A |
| 107 | —Ph | —CH₂C≡CH | —Et | —F | 132–134 | E + H + Y3 + I + A |
| 108 | —Ph | —CH₂C≡CH | —F | —Et | 95–99.5 | D + A |
| 110 | -2,6-diCl-4-pyridyl | —CH₂C≡CH | —Et | —Et | 140–142 | D + A |
| 111 | —Ph | —CH₂C≡CCH=CH₂ | —Et | —CF₃ | 104–106 | B Z12 |
| 112 | —Ph | —CH₂C≡CH | —Et | -3-furyl | 114–115 | D + A |
| 114 | —Ph | —CH₂C≡CH | —Et | -2-thienyl | 133–135 | D + A |
| 115 | —Ph | —Et | —Et | —Et | 61–65 | D + A |
| 116 | -3-PFh | —CH₂C≡CH | —Et | —CF₃ | 102–105 | |

-continued

| Compound No. | R² | R³ | R⁵ | R⁶ | MP °C. | Synthesis |
|---|---|---|---|---|---|---|
| 117 | —Ph | —CH₂C≡CH | —Et | -3-thienyl | 82–85 | D + A |
| 118 | -3-PFh | —CH₂C≡CH | —Et | -i-Pr | 124.5–127.5 | D + A |
| 119 | -3-ClPh | —CH₂C≡CH | —Et | -i-Pr | 112–115 | D + A |
| 120 | —Ph | —CH₂C≡CH | —Et | -4-pyridyl | Oil | D + A |
| 121 | —Ph | —CH₂C≡CH | —Et | -cyclo-Bu | 113–115 | D + A |
| 122 | —Ph | —CH₂C≡CH | —Et | —CH₂Ph | 105–107 | D + A |
| 123 | -3,5-diFPh | —CH₂C≡CH | —Et | —Et | 125–126.5 | D + A |
| 124** | —Ph | —Et | —Et | —Et | Oil | D + A + Z10 |
| 125 | —Ph | —CH₂C≡CH | —Et | —CF₂Cl | 115–117 | D + A |
| 126 | —Ph | —CH₂C≡CH | —Et | -i-Bu | 83–86 | D + A |
| 127 | —Ph | —Me | —Et | —OMe | 90–93 | E + A |
| 128 | —Ph | —CH₂C≡CH | —Et | —OEt | 122–124 | F + A |
| 129 | —Ph | —CH₂C≡CH | —Et | -cyclopropyl | 110–112 | D + A |
| 130 | -3-ClPh | —CH₂C≡CH | —Et | —CF₃ | 123–125 | B |
| 131 | —Ph | —CH₂C≡CH | —Et | —CH=CMe₂ | 94–97 | D + A |
| 132 | -3-BrPh | —CH₂C≡CH | —Et | —Et | 97–99 | D + A |
| 133 | -1-oxo-4-pyridyl | —CH₂C≡CH | —Et | —CF₃ | 129–131 | B + Z8 |
| 134 | -2,6-diCl-4-pyridyl | —CH₂C≡CH | —H | —CF₃ | 149–152 | B |
| 135 | -2,6-diCl-4-pyridyl | —CH₂C≡CH | —Me | —Me | 168–170 | D + A |
| 136 | -2,6-diCl-4-pyridyl | —CH₂C≡CH | —Et | —Me | 138–140 | D + A |
| 137 | -3-CN—Ph | —CH₂C≡CH | —Et | —Et | 115–120 | D + A + Z14 + Z16 + Z17 |
| 138 | -3-(1,3-dioxolan-2-yl)-Ph | —CH₂C≡CH | —Et | —Et | 80.5–83 | D + A |
| 139 | -3-(HON=CH)—Ph | —CH₂C≡CH | —Et | —Et | 190–192 | D + A + Z14 + Z16 |
| 140 | -3-Cl-4-F—Ph | —CH₂C≡CH | —Et | —Et | 80–82 | D + A |
| 141 | -2-CN-4-pyridyl | —CH₂C≡CH | —Et | —CF₃ | 120–122 | B + Z8 + Z9 |
| 142 | -2,6-diMeO-4-pyridyl | —CH₂C≡CH | —Et | —Et | Oil | D + A |
| 143 | -2,6-diCl-4-pyridyl | —CH₂C≡CH | —H | —Et | 132–134 | D + A |
| 144 | -2-MeO-4-pyridyl | —CH₂C≡CH | —Et | —Et | 81–83 | D + A |
| 145 | -2-F-4-pyridyl | —CH₂C≡CH | —Et | —Et | 90–100 | D + A |
| 146 | -2,6-diCl-4-pyridyl | —CH₂C≡CH | —Me | —Et | 147–150 | D + A |
| 147 | -2,6-diCl-4-pyridyl | —CH₂C≡CH | —Et | -n-Pr | 140–142 | D + A |
| 148 | -3-Cl—Ph | —CH₂C≡CH | —Et | -n-Pr | 56–61 | D + A |
| 149 | -3-F—Ph | —CH₂C≡CH | —Et | -n-Pr | 86–87.5 | D + A |
| 150 | -2-CF₃O—Ph | —CH₂C≡CH | —Et | —Et | 55–58 | D + A |
| 151 | -2-Me-4-pyridyl | —CH₂C≡CH | —Et | —Et | 73–75 | D + A |
| 152 | —Ph | —CH₂C≡CH | —Et | -s-Bu | 43–47 | D + A |
| 153 | —Ph | —CH₂C≡CH | —Et | —CHF₂ | 123–124 | B |
| 154 | —Ph | —CH₂C≡CH | —Et | -n-pentyl | 35–39 | D + A |
| 155 | -3,4-diF—Ph | —CH₂C≡CH | —Et | —Et | 75–79 | D + A |
| 156 | -3-CF₃O—Ph | —CH₂C≡CH | —Et | —Et | Oil | D + A |
| 157 | —Ph | —CH₂C≡CH | —Et | -cyclopentyl | 120–123 | D + A |
| 158 | -4-pyridyl | —CH₂C≡CH | —Et | —Et | 116–119 | D + A |
| 159 | -3-F—Ph | —CH₂C≡CH | —Et | —Cl | 80–82 | E + H + I + A |
| 160 | -3-pyridyl | —CH₂C≡CH | —Et | —Et | 92–94 | D + A |
| 161 | -3-Cl—Ph | —CH₂C≡CH | —Et | Cl | 103–106 | E + H + I + A |
| 162 | -1-oxo-4-pyridyl | —CH₂C≡CH | —Et | —Et | 127–130 | D + A + Z8 |
| 163 | -3-Cl—Ph | —CH₂C≡CH | —Et | —Me | 90–92 | D + A |
| 164 | -3-Cl—Ph | —CH₂C≡CH | —Et | —Et | 123–125 | D + A |
| 165 | -1-oxo-3-pyridyl | —CH₂C≡CH | —Et | —Et | 108–111 | D + A + Z8 |
| 166 | -3,4,5-triF—Ph | —CH₂C≡CH | —Et | —Et | 113–114 | D + A |
| 167 | 2-Cl—Ph | —CH₂C≡CH | —Et | —Et | 91–93.5 | D + A |
| 168 | —Ph | —CH₂C≡CH | —Et | -n-C₇H₁₅ | 63–66 | D + A |
| 169 | -6-Cl-2-pyridyl | —CH₂C≡CH | —H | —CF₃ | 120–121 | B |
| 170 | -4-Cl-2-thienyl | —CH₂C≡CH | —Et | —Et | 134–137 | D + A |
| 171 | -2-thienyl | —CH₂C≡CH | —Et | —Et | 135–136.5 | D + A |
| 172 | —Ph | —CH₂C≡CH | —Cl | —Et | 112–114 | D + Y4 + A |
| 173 | -2,6-diF-4-pyridyl | —CH₂C≡CH | —H | —CF₃ | 135–137 | B |
| 174 | -5-Cl-2-thienyl | —CH₂C≡CH | —Et | —Et | 131–133 | D + A |
| 175 | —Ph | —CH₂C≡N | —Et | —Et | 239–240 | D + A |
| 176 | -2,6-diCl-4-pyridyl | —CH₂C≡CH | —Me | —CF₃ | 131–134 | B |
| 177 | -5-Cl-3-thienyl | —CH₂C≡CH | —Et | —Et | 134–136.5 | D + A |
| 178 | -2,5-diCl-3-thienyl | —CH₂C≡CH | —Et | —Et | Oil | D + A |
| 179 | —Ph | —CH₂COCH₃ | —Et | —CF₃ | 131–133 | B + Z3 |
| 180 | -5-Cl-3-pyridyl | —CH₂C≡CH | —Et | —Et | Oil | D + A |
| 181 | —Ph | cis & trans —CH₂CH=CHCl | —Et | —Et | Oil | D + A |
| 182 | —Ph | —CH₂C≡CSiMe₃ | —Et | —Et | Oil | D + A + Z11 |
| 183 | —Ph | —CH₂C≡CH | —OMe | —Et | 131–132.5 | D + A |
| 184 | -3-F-5-CF₃—Ph | —CH₂C≡CH | —Et | —Et | 64–66 | D + A |
| 185 | —Ph | —Et | —CF₃ | —Et | 81–83 | D + Y2 + A + Z15 |
| 207 | -3-furyl | —CH₂C≡CH | —Et | —Et | 117–119 | D + A |
| 212 | -3-Cl-4-Me—Ph | —CH₂C≡CH | —H | —CF₃ | 148–150 | B |
| 215 | -3,5-diCl-4-Me—Ph | —CH₂C≡CH | —H | —CF₃ | 113–115 | B |
| 219 | —Ph | —CH₂C≡Cl | —Et | —CF₃ | 120–125 | B + Z18 |
| 220 | -3,5-diCl-4-F—Ph | —CH₂C≡CH | —H | —CF₃ | — | B |

The following ¹H-NMR data is provided for compounds in the above table which were oils or solids

| Compound No. | $^1$H-NMR |
|---|---|
| 11 | 1.25(9H, s), 2.35(1H, t), 4.6(2H, d), 6.4(1H, s), 7.55(3H, m), 7.7(2H, m) |
| 18 | 4.6(2H, m), 5.0(1H, dd), 5.25(1H, dd), 5.9(1H, m), 6.9(1H,s), 7.55(5H, m) |
| 20 | 1.25(3H, t), 4.0(2H, q), 6.85(1H, s), 7.5(5H, m) |
| 62 | 1.25(3H, t), 2.5(1H, t), 2.80(2H, q), 4.65(2H, d), 7.35(1H, s), 7.6(1H, d), 8.5(1H, d) |
| 67 | 1.15(3H, t), 1.2(6H, d), 2.5(1H, t), 2.65(2H, q), 3.15(1H, m), 4.6(2H, d), 7.65(2H, s) |
| 81 | 2.4(1H, t), 4.3(2H, s), 4.6(2H, d), 6.65(1H, s), 7.55(3H, m), 7.7(2H, m) [6-CH$_2$Br] 2.4(1H, t), 4.4(2H, s), 4.6(2H, d), 6.71(1H, s), 7.55(3H, m), 7.7(2H, m) [6-CH$_2$Cl] |
| 92 | 0.25(9H, s), 1.25(3H, t), 2.37(1H, t), 2.85(2H, q), 4.60(2H, d), 7.55(3H, m), 7.75(2H, m) |
| 120 | 1.25(3H, t), 2.43(1H, t), 2.61(2H, q), 4.68(2H, d), 7.5(2H, d), 7.55(3H, m), 7.75(2H, m), 8.75(2H) |
| 124 | 1.25(9H, m), 2.7(2H, q), 3.08(2H, q), 4.62(2H, q), 7.5(5H, m) |
| 142 | 1.15(3H, t), 1.25(3H, t), 2.35(1H, t), 2.60(4H, q), 3.95(6H, s), 4.55(2H, d), 6.55(2H, s). |
| 156 | 1.25(6H, m), 2.4(1H, t), 2.65(4H, q), 4.6(2H, d), 7.35–7.75(4H, m) |
| 178 | 1.35(6H, m), 2.78(4H, m), 2.95(1H, t), 4.9(2H, d), 8.2(1H, s) |
| 180 | 1.20(3H, t), 1.25(3H, t), 2.45(1H, t), 2.65(4H, q), 4.60(2H, d), 8.10(1H, s), 8.75(1H, s), 8.85(1H, s). |
| 181 | 1.2(6H, m), 2.65(4H, m), 4.5(2H, m), 5.95(2H, m), 7.5(5H, m), {cis} 1.2(6H, m), 2.65(4H, m), 4.7(2H, m), 5.95(1H, m), 6.15(1H, m), 7.5(5H, m) {trans} |
| 182 | 0.18(9H, s), 1.25(6H, m), 2, 65(4H, q), 4.6(2H, s), 7.42–7.8(5H, m) |
| 220 | 2.5(1H, t), 4.6(2H, d) 6.9(1H, s), 7.8(2H, d) |

The following table of compounds are additional compounds listed as examples within the embodiment of the present invention:

TABLE 2

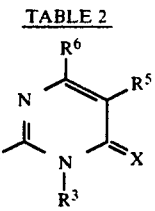

For the below table, "Me" is methyl, "Et" is ethyl, "Pr" is propyl and "Ph" is phenyl. For the compounds, X is preferably oxygen.

| No | R$^2$ | R$^3$ | R$^5$ | R$^6$ |
|---|---|---|---|---|
| 186 | —Ph | —CH$_2$C≡CH | —CF$_3$ | —Et |
| 187 | —Ph | —CH$_2$C≡CH | —Et | —CN |
| 188 | —Ph | —CH$_2$C≡CH | —CH$_2$F | —Et |
| 189 | —Ph | —CH$_2$C≡CH | —OMe | -i-Pr |
| 190 | —Ph | —CH$_2$C≡CH | —OMe | -n-Pr |
| 191 | —Ph | —CH$_2$C≡CH | —OMe | —Cl |
| 192 | -2,6-diCl-4-pyridyl | —CH$_2$C≡CH | —Et | —Cl |
| 193 | -2-CF$_3$-4-pyridyl | —CH$_2$C≡CH | —Et | —Et |
| 194 | -4-Cl-2-pyridyl | —CH$_2$C≡CH | —Et | —Et |
| 195 | -4,6-diCl-2-pryidyl | —CH$_2$C≡CH | —Et | —Et |
| 196 | -2-pyridyl | —CH$_2$C≡CH | —Et | —Et |
| 197 | -2-naphthyl | —CH$_2$C≡CH | —Et | —Et |
| 198 | -2,6-diF-4-pyridyl | —CH$_2$C≡CH | —Et | —Et |
| 199 | -2,6-diCl-4-pyridyl | —CH$_2$C≡CH | —OMe | —Et |
| 200 | —Ph | —CH$_2$C≡CH | —Et | —C(CH$_3$)=CH$_2$ |
| 201 | —Ph | —CH$_2$C≡CH | —Et | —CH$_2$C≡CH |
| 202 | —Ph | —CH$_2$C≡CH | —Et | —CH$_2$CH=CH$_2$ |
| 203 | —Ph | —CH$_2$C≡CH | —Et | —OPh |
| 204 | —Ph | —CH$_2$C≡CH | —Et | —OMe |
| 205 | —Ph | —CH$_2$C≡CH | —Et | —OCHF$_2$ |
| 206 | —Ph | —CH$_2$C≡CH | —OCHF$_2$ | —Et |
| 208 | -5-Cl-3-furyl | —CH$_2$C≡CH | —Et | —Et |
| 209 | -3-F—Ph | —CH$_2$C≡CH | —H | —CF$_3$ |
| 210 | -3,5-diCl—Ph | —CH$_2$C≡CH | —H | —CF$_3$ |
| 211 | -3,5-diF—Ph | —CH$_2$C≡CH | —H | —CF$_3$ |
| 213 | -3-Cl-4-F—Ph | —CH$_2$C≡CH | —H | —CF$_3$ |
| 214 | -3,4-diF—Ph | —CH$_2$C≡CH | —H | —CF$_3$ |
| 216 | -3,4-methylenedioxy-Ph | —CH$_2$C≡CH | —Et | —Et |
| 217 | -5-Cl-3-thienyl | —CH$_2$C≡CH | —Et | —CF$_3$ |
| 218 | -3,4,5-triF—Ph | —CH$_2$C≡CH | —Et | —CF$_3$ |

METHODS OF PREPARATION

The 2-arylpyrimidines of the present invention may be prepared by standard synthetic routes such as those illustrated below.

Method A—General Description

A precursor compound having the structure of formula I above with hydrogen (H) in the R$^3$ substituent position is selected. Reaction with R$^3$Y is performed in a base-solvent mixture. Y can be a halogen, alkanesulfonate, haloalkanesulfonate or optionally substituted benzenesulfonate. The bases can be sodium hydride, alkali metal hydroxides, alkali metal carbonates or alkali metal alkoxides. The solvent can be alcohol, ketone, water, ether, DMSO or DMF. A mixture of N- and O-alkylated products results.

Method A—Specific Example—Preparation of 6-ethyl-5-methyl-2-phenyl-3-propargyl-4(3H)-pyrimidinone To a stirred solution of 24.30 g (0.45 mol) of sodium methoxide in 400 mL of methanol was added a slurry of 61.78 g (0.29 mol) of 6-ethyl-5-methyl-2-phenyl-4(3H)-pyrimidinone in 100 mL of methanol. The mixture was heated to reflux to give a clear orange solution to which 44.89 g (0.30 mol) of an 80% weight solution of propargyl bromide in toluene was added. The course of the reaction was followed by GC. Refluxing was continued for 6.5 h, when an additional 20.63 g (0.14 mol) of an 80% weight solution of propargyl bromide in toluene was added. Refluxing was continued for an additional 4.5 h. The reaction mixture was allowed to cool to room temperature and 250 mL of water and 250 mL of saturated aqueous NaHCO$_3$ were added. The mixture was rotovaped to remove the bulk of the methanol and extracted with three 200 mL portions of ethyl acetate. The ethyl acetate extracts were combined, filtered and extracted with three 200 mL portions of 5% aq HCl. The combined aqueous HCl extracts were basified to pH 11 with 50% aqueous NaOH and extracted with three 250 mL portions of ether. The combined ether extracts were washed with 100 mL of brine, dried over MgSO$_4$ and rotovaped to leave 30.46 g of a yellowish solid. This material was triturated with 100 mL portions of 10, 25 and 50% ether in hexanes and recrystallized from 25 mL of toluene to furnish 15.11 g. of Compound 5 as a white solid mp 115°–117° C. $^1$H-NMR (d$^6$-DMSO) δ1.15(3H, t, J=7.8), 2.07(3H, s), 2.58(2H, q, J=7.8), 3.32(1H, t, J=2.4), 4.55(2H, d, J=2.4), 7.58(3H, m), 7.65(2H, m).

Method B—General Description

Direct condensation of an N-alkylamidine and a beta-keto ester is performed by warming the reagents in a solvent such as THF or neat: R$^2$C(=NH)N(H)R$^3$+R$^6$C(=O)CH(R$^5$)C(=O)OR→2-arylpyrimidine (FIG. I) Preferably R$^3$ is a non-reactive group and when R$^3$ is a propargyl group, preferably R$^6$ is CF$_3$.

Method B—Specific Example—Preparation of 5-ethyl-2-phenyl-3-propargyl-6-trifluoromethyl-4(3H)-pyrimidinone To a stirred solution of 22.66 g (0.13 mol) of methyl benzimidate hydrochloride in 80 mL of methanol was added 11.09 g (0.13 mol) of powdered sodium bicarbonate. The mixture was stirred for 0.5 h and 9.1 mL (0.13 mol) of propargylamine was added. The mixture was stirred for 4 h at room temperature and then rotovapped to remove most of the methanol. To the oily orange residue was added 34.00 g of 80% pure ethyl 2-trifluoroacetylbutyrate (0.13 mol). The mixture was heated at 55°–60° C. for 40 h. The mixture was diluted with 300 mL of ether, washed with two 150 mL portions of 5% aqueous HCl and 150 mL of saturated aqueous sodium bicarbonate and dried over MgSO$_4$. Removal of the solvent and drying at 50° C. under high vacuum afforded 22.58 g of an orange solid. This material was purified by flash chromatography on 325 g of silica gel, eluting with 0, 10, 20, 30 and finally 40% ether in hexanes to furnish 16.86 g of a yellow solid. This material was triturated with two 100 mL portions of boiling hexanes and recrystallized from 150 mL of 10% ether in hexanes to give 10.31 g (26%) of 5-ethyl-2-phenyl-3-propargyl-6-trifluoromethyl-4(3H)-pyrimidinone (Compound No. 46) as a white solid, mp 111°–114° C. $^1$H-NMR (CDCl$_3$) δ1.24(3H,t), 2.38(1H,t), 2.75(2H,q), 4.62(2H,d), 7.55(3H,m), 7.74(2H,m).

Method D—General Description

An amidine hydrochloride or other salt is heated with a beta-keto ester in a solvent in the presence of a base to neutralize the hydrochloric acid. Solvents usable include xylene or toluene, preferably, or ethanol or heptane. Sodium acetate or sodium ethoxide can be the base:

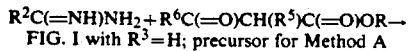

FIG. I with R$^3$=H; precursor for Method A

Method D—Preparation of 6-ethyl-5-methyl-2-phenyl-4(3H)-pyrimidinone

A 2L 3-neck flask equipped with mechanical stirrer, Dean Stark trap and a reflux condenser was purged with nitrogen and charged with 93.91 g. (0.59 mol) of methyl 2-propionylpropionate, 103.58 g (≦0.66 mol) of benzamidine hydrochloride hydrate, 54.30 g (0.66 mol) of anhydrous sodium acetate and 1L of xylenes. The mixture was stirred and heated to reflux under a nitrogen atmosphere for 46 h.

The Dean Stark trap was replaced with a distillation head and about 75% of the solvent was distilled off at atmospheric pressure. After the flask had cooled to room temperature, 500 mL of water and 200 mL of ether were added. The mixture was filtered and the solid collected was washed thoroughly with water and ether and dried in a vacuum oven at 60° C. to give 74.73 g (50%) of the desired product, mp 195°–199° C. $^1$H-NMR (d$^6$-DMSO) δ1.23(3H, t, J=7.8), 2.02(3H, s), 2.61(2H, q, J=7.8), 7.50(3H, m), 8.13(2H, m).

The filtrate was separated into aqueous and organic layers. The organic layer was extracted with three 125 mL portions of 5% aqueous NaOH. The combined aqueous base extracts were acidified to pH 7 with aqueous HCl, allowed to cool and filtered. The solid collected was washed with water and ether and dried in a vacuum oven at 60° C. to afford an additional 5.16 g (4%) of the desired product, mp 196°–199° C.

Method E—General Description

Malonate diester is condensed with an amidine under basic conditions. For example, sodium methoxide in refluxing methanol may be used:

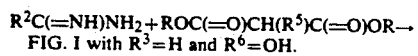

FIG. I with R$^3$=H and R$^6$=OH.

Method E—Preparation of 5-ethyl-6-hydroxy-2-phenyl-4(3H)-pyrimidinone

A mixture of 45.19 g (0.29 mol) of benzamidine hydrochloride hydrate, 127.42 g (0.59 mol) of 25% sodium methoxide in methanol, 55 mL (0.29 mol) of diethyl ethylmalonate and 175 mL of methanol was heated at reflux for 25 h. The mixture was rotovapped to remove the bulk of the methanol. The residue was diluted with 300 mL of water and the pH was adjusted to 7 with concentrated hydrochloric acid. The solid precipitate was collected by filtration and dried under vacuum at 50° C. to afford 31.89 g (51%) of crude 5-ethyl-6-hydroxy-2-phenyl-4(3H)-pyrimidinone as a pale yellow solid. $^1$H-NMR (d6-DMSO) δ1.05(3H,t), 2.39(2H,q), 7.5(3H,m), 8.1(2H,m).

Method F—General Description

Method F is similar to Method D except that a 3-alkoxyacrylate ester is used instead of a beta-keto ester:

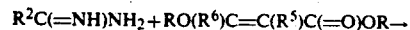

FIG. I with R$^3$=H

Various conditions are usable: for example, amidine hydrochloride/3-alkoxyacrylate in NaOAc/DMSO at 120 degrees Centrigrade or in sodium methoxide/ethanol at 5 degrees Centigrade.

Method F—Specific Example—Preparation of 6-ethoxy-2-phenyl-4(3H)-pyrimidinone

A mixture of 3.14 g (20.0 mmol) of benzamidine hydrochloride hydrate, 1.65 g (20.1 mmol) of powdered anhydrous sodium acetate, 4.17 g (22.2 mmol) of ethyl 3,3-diethoxyacrylate and 10 mL of DMSO was heated at 120° C. for 8 h. The mixture was cooled, diluted with 50 mL of 5% aqueous NaOH and washed with two 100 mL portions of ether. The aqueous layer was acidified with concentrated hydrochloric acid and the precipitate was collected by filtration and dried under vacuum at 50° C. to furnish 2.28 g (57%) of crude 6-ethoxy-2-phenyl-4(3H)-pyrimidinone as a yellow solid $^1$H-NMR (d6-DMSO) δ1.35(3H,t), 4.33(2H,q), 5.60(1H,s), 7.50(3H,m), 8.2(2H,m).

Method H—General Description

6-Hydroxy-4(3H)-pyrimidinones were heated with phosphorus oxyhalide with or without a cosolvent to give 6-halo-4(3H)-pyrimidinones. For example, phosphorous oxybromide was used with an inert solvent (1,2-dichloroethane) at reflux. See U.S. Pat. No. 4,617,393.

Method H—Specific Example—Preparation of 4,6-dibromo-5-ethyl-2-phenylpyrimidine

A mixture of 24.50 g (85.3 mmol) of phosphorus oxybromide, 7.56 g (37.3 mmol) of 5-ethyl-6-hydroxy-2-phenyl-4(3H)-pyrimidinone and 20 mL of 1,2-dichloroethane was heated at reflux for 2 h. After cooling to room temperature, the mixture was poured onto 300 g of crushed ice. The ice was allowed to melt, the mixture was basified by cautious addition of solid Na$_2$CO$_3$ and then extracted with two 200 mL portions of ethyl acetate. The combined ethyl acetate extracts were dried over MgSO$_4$ and concentrated to afford 11.79 g (92%) of crude 4,6-dibromo-5-ethyl-2-phenylpyrimidine. This material was recrystallized from hexanes to furnish 6.62 g (52%) of pure product, mp 101°–103° C. $^1$H-NMR (CDCl$_3$) δ1.20(3H,t), 2.95(2H,q), 7.45(3H,m), 8.35(2H,m).

Method I—General Description 4,6-dihalopyrimidines are acidically hydrolyzed to give 6-halo-4(3H)-pyrimidinones. See U.S. Pat. No. 4,617,393.

Method I—Specific Example—Preparation of 6-bromo-5-ethyl-2-phenyl-4(3H)-pyrimidinone To 8.29 g (26.1 mmol) of crude 4,6-dibromo-5-ethyl-2-phenylpyrimidine was added a mixture of 4 mL of water and 15 mL of concentrated sulfuric acid. The mixture was stirred for 18 h and poured onto 200 g of crushed ice. After the ice had melted the precipitate was collected by filtration and dried under vacuum to afford 7.21 g (99%) of crude 6-bromo-5-ethyl-2-phenyl-4(3H)-pyrimidinone. $^1$H-NMR (d6-DMSO) δ1.10(3H,t), 2.55(2H,q), 7.55(3H,m), 8.10(2H,m).

Method Y1

(a) Preparation of 5-bromo-2-phenyl-6-trifluoromethyl-4(3H)-pyrimidinone.

To a solution of 1.0 g (3.94 mmol) of 2-phenyl-6-trifluoromethyl-4(3H)-pyrimidinone and 20 mL of glacial acetic acid was added 1.0 g (5.6 mmol) N-bromosuccinimide and the mixture was left to stir at room temperature for 16 h. The reaction was poured onto ice water and vacuum filtered, washing well with water. The crude product was recrystallized from ethyl acetate to yield 1.05 g (83.5%) of 5-bromo-2-phenyl-6-trifluoromethyl-4(3H)-pyrimidinone, as a white solid. $^1$H-NMR (d6DMSO) δ7.6 (3H, m); 8.15 (2H, m).

(b) Preparation of 5-bromo-2,6-diphenyl-4(3H)-pyrimidinone.

To a suspension of 13.37 g (56 mmol) of 2,6-diphenyl-4(3H)-pyrimidinone and 200 mL glacial acetic acid was added 15.1 g (84.8 mmol) of N-bromosuccinimide and the mixture was left to stir at room temperature for 60 h. The reaction was poured onto 100 g crushed ice and vacuum filtered, washing well with water, then air dried to yield 8.85 g (48%) 5-bromo-2,6-diphenyl-4(3H)-pyrimidinone, as a white solid. $^1$H-NMR (d6DMSO) δ7.55 (6H, m); 7.75 (2H, m); 8.15 (2H, m).

Method Y2—Preparation of 6-ethyl-5-iodo-2-phenyl-4(3H)-pyrimidinone

A mixture of 8.18 g (40.9 mmol) of 6-ethyl-2-phenyl-4(3H)-pyrimidinone, 1.68 g (42.0 mmol) of sodium hydroxide, 10.42 g (41.0 mmol) of iodine and 50 mL of water was heated at 50° C. for 4 h. The mixture was cooled and filtered. The white solid collected was dried in a vacuum oven to leave 12.60 g (75%) of 6-ethyl-5-iodo-2-phenyl-4(3H)-pyrimidinone. $^1$H-NMR (d6-DMSO) δ1.25(3H,t), 2.85(2H,q), 7.50(3H,m), 8.15(2H,m).

Method Y3—Preparation of 4,6-difluoro-5-ethyl-2-phenyl-pyrimidinone

To a stirred solution of 3.14 g (12.41 mmol) portion of 4,6-dichloro-5-ethyl-2-phenylpyrimidine in 25 mL of sulfolane at 70°–80° C. was added 6.37 g (109.8 mmol) of spray-dried potassium fluoride. The mixture was heated at 200° C. for 0.5 h. After cooling, the mixture was diluted with 100 mL of water and extracted with 400 mL of 1:1 ether:hexanes. The organic layer was washed with two 100 mL portions of water, dried over MgSO$_4$ and concentrated to give 2.30 g of crude product. This material was combined with 0.29 g of crude product from another run and purified by flash chromatography on a column of 40 g of silica gel. The column was eluted with 0, 5, 10, 15 and 20% ether in hexanes to furnish 2.18 g (71%) of 4,6-difluoro-5-ethyl-2-phenyl-pyrimidine as a white solid, m.p. 49°–51° C. $^1$H-NMR (CDCl$_3$) δ1.2(3H,t), 2.65(2H,q), 7.50(3H,m), 8.4(2H,m).

Method Y4—Preparation of 5-Chloro-6-ethyl-2-phenyl-4(3H)-pyrimidinone

A stirred solution of 7.81 g (39.1 mmol) of 6-ethyl-2-phenyl-4(3H)-pyrimidinone and 5.80 g (43.4 mmol) of N-chlorosuccinimide in 100 mL of glacial acetic acid was heated at 90° C. for 4 h. The mixture was cooled, poured onto crushed ice and allowed to stand until the ice had melted. The mixture was filtered and the solid collected was washed with water and a little ether. The solid was dried in a vacuum oven at 50 C. to afford 7.99 g of 5-chloro-6-ethyl-2-phenyl-4(3H)-pyrimidinone (an intermediate for compound 172) as a white solid. $^1$H-NMR (d6-DMSO) 1.30(3H,t), 2.8(2H,q), 7.6(3H,m), 8.2(2H.m).

Method Z1—Preparation of 6-dimethylaminocarbonyl-5-methyl-2-phenyl-3-propargyl-4(3H)-pyrimidinone. (Compound 19)

To a solution of 1.81 g (6.1 mmol) of 6-ethoxycarbonyl-5-methyl-2-phenyl-3-propargyl-4(3H)-pyrimidinone in 100 mL of ethanol and 50 mL of THF was added 50 mL of 5% aqueous sodium hydroxide. The mixture was stirred at room temperature for 24 h and rotovapped to remove the bulk of the organic solvents. The residue was diluted with 50 mL of 5% aqueous sodium hydroxide and washed with 100 mL of ether. The aqueous phase was acidified with concentrated hydrochloric acid and extracted with two 100 mL portions of ethyl acetate. The combined ethyl acetate extracts were washed with 50 mL of brine, dried over $MgSO_4$ and concentrated to leave 0.87 g (53%) of crude 6-carboxy-5-methyl-2-phenyl-3-propargyl-4(3H)-pyrimidinone as a brown oil.

To a stirred solution of 0.87 g (3.2 mmol) of crude 6-carboxy-5-methyl-2-phenyl-3-propargyl-4(3H)-pyrimidinone, 0.32 g (3.9 mmol) of dimethylamine hydrochloride and 2 mL of pyridine in 10 mL of THF was added 0.74 g (3.6 mmol) of solid N,N'-dicyclohexylcarbodiimide. The mixture was stirred at room temperature for 4 days and filtered to remove insoluble material. The filtrate was diluted with 150 mL of ethyl acetate, washed with 50 mL of 5% aqueous HCl and 50 mL of saturated aqueous sodium bicarbonate and dried over $MgSO_4$. Removal of the solvent left 0.40 g of crude product which was purified by flash chromatography on a 30 g column of silica gel, eluted with 60, 80 and 100% ethyl acetate in hexanes to furnish 0.30 g (32%) of 6-dimethylaminocarbonyl-5-methyl-2-phenyl-3-propargyl-4(3H)-pyrimidinone (compound 19), mp 137°–140° C. $^1$H-NMR (CDCl$_3$) δ2.15(3H,s), 2.40(1H,t), 3.00(3H,s), 3.10(3H,s), 4.65(2H,d), 7.55(3H,m), 7.70 (2H,m).

Method Z2—Preparation of 6-dimethylamino-5-methyl-2-phenyl-3-propargyl-4(3H)-pyrimidinone. (Compound 23)

To an ice cooled solution of 1.5 g (3.8 mmol) 6-chloro-5-methyl-2-phenyl-3-propargyl-4(3H)-pyrimidinone in 4 mL of tetrahydrofuran, was added 22 mL (99 mmol) of 4.5M dimethylamine in ether portionwise (2–4 mL) over a period of 7 days. The reaction mixture was allowed to warm and stir at room temperature after each addition. The progress of the reaction was followed by gas chromatography and proceeded to 80% completion. The solvent was removed in vacuo and the residue was taken up in ether and washed twice with water. The organic layer was dried over $MgSO_4$ and concentrated to yield 1.15 g crude solid product. Flash column chromatography on silica gel (gradient elution 25–30% ethyl acetate-hexane) afforded pure 6-dimethylamino-5-methyl-2-phenyl-3-propargyl-4(3H)-pyrimidinone (compound 23), as a white solid. $^1$H-NMR (CDCl$_3$) δ2.2 (3H, s); 2.35 (1H, t); 3.5 (6H, s); 4.6 (2H, d); 7.65 (3H, m); 7.75 (2H, m).

Method Z3—Preparation of 5-Ethyl-3-(2-oxopropyl)-2-phenyl-6-trifluoromethyl-4(3H)-pyrimidinone (Compound 179)

To a stirred solution of 4.83 g (15.8 mmol) of 5-ethyl-3-propargyl-2-phenyl-6-trifluoromethyl-4(3H)-pyrimidinone (compound 46) in 50 mL of THF was added 50 mL of 10% aq NaOH. The mixture was heated at reflux for 2 h, cooled and diluted with 150 mL of ethyl acetate. The organic layer was separated, washed with 50 mL of water and 50 mL of brine and dried over $MgSO_4$. Removal of the solvent afforded 4.74 g of 5-ethyl-3-(2-oxopropyl)-2-phenyl-6-trifluoromethyl-4(3H)-pyrimidinone (compound 179) as a white solid. $^1$H-NMR (CDCl$_3$) 1.2(3H), 2.2(3H,s), 2.7(2H,q), 4.7(2H,s), 7.45(5H,m).

Method Z4—Preparation of 5-methyl-2-phenyl-3-propargyl-6-methylthio-4(3H)-pyrimidinone. (Compound 26)

To a solution of 2.5 g (9.67 mmol) of 6-chloro-5-methyl-2-phenyl-3-propargyl-4(3H)-pyrimidinone in 100 mL of methanol, was added 0.8 g (11.4 mmol) sodium thiomethoxide and the reaction was stirred at room temperature for 4 days. The methanol was evaporated and the residue was dissolved in 100 mL of ethyl acetate, then washed three times with 50 mL of 1M sodium hydroxide followed by one time with 50 mL of brine. The organic layer was dried over $MgSO_4$ and concentrated to yield 2.6 g crude product. Flash column chromatography on silica gel (100% methylene chloride) afforded 5-methyl-2-phenyl-3-propargyl-6-thiomethyl-4(3H)-pyrimidinone (Compound 26) as a white solid. $^1$H-NMR (CDCl$_3$) δ2.1 (3H, s); 2.35 (1H, t); 2.5 (3H, s); 4.55 (2H, d); 7.5 (3H, m); 7.7 (2H, m).

Method Z5—Preparation of 3-(2,2-dimethoxypropyl)-6-ethyl-5-methyl-2-phenyl-4(3H)-pyrimidinone (Compound 36)

To a stirred suspension of 4.51 g (17.9 mmol) of 6-ethyl-5-methyl-2-phenyl-3-propargyl-4(3H)-pyrimidinone (Compound 5) in 30 mL of methanol was added 7.50 g (34.7 mmol) of a 25% by weight solution of sodium methoxide in methanol. The mixture was warmed until homogeneous and 2.2 mL (35.3 mmol) of methyl iodide was added. The mixture was refluxed for 4 h and then rotovapped to remove the bulk of the methanol. The residue was partitioned between 100 mL of water and two 100 mL portions of ether. The combined ether layers were washed with 50 mL of brine and dried over $MgSO_4$. Removal of the solvent afforded 4.35 g of a yellow oil. Flash chromatography on a column of 50 g of silica gel, eluting with 20, 30, 40 and 50% ether in hexanes furnished 3.30 g (58%) of 3-(2,2-dimethoxypropyl)-6-ethyl-5-methyl-2-phenyl-4(3H)-pyrimidinone (compound 36), mp 80°–83° C. $^1$H-NMR (CDCl$_3$) δ1.15(3H,s), 1.25(3H,t), 2.15(3H,s), 2.65(2H,q), 2.85(6H,s), 4.4(2H,m), 7.45(5H,s).

Method Z6—Preparation of 3-methoxymethyl-2-phenyl-6-trifluoromethyl-4(3H)-pyrimidinone (Compound 6)

To a solution of 1.5 g (5.9 mmol) of 2-phenyl-6-trifluoromethyl-4(3H)-pyrimidinone, 17.2 g (226.3 mmol) dimethoxymethane, and 35 mL of chloroform was added 2.5 g (17.6 mmol) phosphorous pentoxide, at room temperature. By TLC (25% ethyl acetate in hexane) the reaction was incomplete after 4 h and an additional 3 g (21.1 mmol) phosphorous pentoxide was added. Stirring was continued for 16 h. The reaction mixture was poured onto crushed ice and 1M sodium hydroxide and methylene chloride were added. The layers were separated and the aqueous layer was extracted twice with methylene chloride. The organic extracts were combined and washed with brine, then dried over $MgSO_4$ and concentrated to yield 1.1 g crude product, which was purified by recrystallization from hexane. Thus, 0.55 g (32%) 3-methoxymethyl-2-phenyl-6-trifluoromethyl-4(3H)-pyrimidinone (Compound 6) as a yellow solid was obtained. $^1$H-NMR (CDCl$_3$) δ3.55 (3H, s); 5.2 (2H, d); 6.85 (1H, s); 7.65 (3H, m); 7.75 (2H, m).

Method Z7—Preparation of 6-ethyl-2-phenyl-3-propargyl-5-(2-trimethylsilylethynyl)-4(3H)-pyrimidinone (Compound 92)

To a stirred solution of 3.59 g (9.86 mmol) of 6-ethyl-5-iodo-2-phenyl-3-propargyl-4(3H)-pyrimidinone and 16.45 g (167.5 mmol) of trimethylsilylacetylene in 40 mL of DMF were added 1.13 g (0.98 mmol) of tetrakis(triphenylphosphine) palladium(0), 0.41 g (2.15 mmol) of copper (I) iodide and 2.8 mL (20.0 mmol) of triethylamine. The mixture was stirred at room temperature for 18 h, diluted with 200 mL of water and extracted with two 200 mL portions of ether. The combined ether extracts were dried over MgSO$_4$ and evaporated under reduced pressure to leave 5.71 g of a black oil. This material was subjected to flash chromatography on a column of 50 g of silica gel, eluted with 0, 10, 20, 30, 40, 50, 60 and 80% ether in hexanes to afford 0.80 g of material. Further purification was effected by chromatography on a column of activity I alumina eluted with 0, 10, 20, 35, 50, 75 and 100% ether in hexanes. This process yielded 0.43 g (13%) of 6-ethyl-2-phenyl-3-propargyl-5-(2-trimethylsilylethynyl)-4(3H)-pyrimidinone as an oil. $^1$H-NMR (CDCl3) δ0.25(9H,s), 1.25(3H,t), 2.37(1H,t), 2.85(2H,q), 4.60(2H,d), 7.55(3H,m), 7.75(2H,m).

Method Z8—5-Ethyl-2-(1-oxo-4-pyridyl)-3-propargyl-6-trifluoromethyl-4(3H)-pyrimidinone (Compound 133)

To a stirred suspension of 8.54 g (27.8 mmol) of -5-ethyl-3-propargyl-2-(4-pyridyl)-6-trifluoromethyl-4(3H)-pyrimidinone (compound 58) in 50 mL of ethanol was added 9.07 g (18.3 mmol) of monoperoxyphthalic acid magnesium salt hexahydrate. The mixture was stirred at room temperature for 24 h. The bulk of the ethanol was removed on the rotovap and the residue was partitioned between 150 mL of ethyl acetate and 75 mL of 5% aqueous hydrochloric acid. The organic layer was washed with two 75 mL portions of saturated aqueous NaHCO$_3$, dried MgSO$_4$ and concentrated to leave 8.42 g of 5-ethyl-2-(1-oxo-4-pyridyl)-3-propargyl-6-trifluoromethyl-4(3H) -pyrimidinone (compound 133) as a yellow solid. $^1$H-NMR (CDCl$_3$) 1.25(3H,t), 1.30(3H,t), 2.60(1H,t), 2.8(4H,m), 4.7(2H,d), 7.8(2H,d), 8.35(2H,d).

Method Z9—Preparation of 2-(2-Cyano-4-pyridyl)-5-ethyl-3-propargyl-6-trifluoromethyl-4(3H) -pyrimidinone (Compound 141)

To a stirred solution of 6.96 g (21.6 mmol) of 5-ethyl-2-(1-oxo-4-pyridyl)-3-propargyl-6-trifluoromethyl-4(3H)-pyrimidinone and 6.0 mL (42.8 mmol) of triethylamine in 20 mL of acetonitrile was added 11.5 mL (86.3 mmol) of trimethylsilyl cyanide. The mixture was heated at reflux for 4 h. After standing overnight, the mixture was diluted with 150 mL of ether, washed with three 50 mL portions of water and dried over MgSO$_4$. Removal of the solvent left 4.94 g of crude product as a black tar. This material was purified by flash chromatography on 60 g of silica gel, eluting with 0, 20, 35, 50, 65, 80 and 100% ether in hexanes to furnish 1.78 g of 2-(2-cyano-4-pyridyl)-5-ethyl-3-propargyl-6-trifluoromethyl-4(3H)-pyrimidinone (compound 141) as a solid. $^1$H-NMR (CDCl$_3$) 1.25(3H,t), 2.60(1H,t), 2.8(2H,q), 4.6(2H,d), 8.0(1H,d), 8.0(1H,s), 9.0(1H,d).

Method Z10—Preparation of 2-phenyl-3,5,6-triethyl-4(3H)-pyrimidinethione (Compound 124)

A mixture of 1.0 g (3.9 mmol) 2-phenyl-3,5,6-triethyl-4(3H)-pyrimidinone, 0.87 g (2.1 mmol) Lawesson's reagent and 35 mL toluene was refluxed for 20 h. By TLC (20% ethyl acetate-hexane) the product was more polar than the starting material. The reaction was incomplete and an additional 1.2 g (2.96 mmol) of Lawesson's reagent was added and refluxing was continued for 16 h. The solvent was removed in vacuo to leave 2.2 g yellow wet solid. Flash column chromatography on silica gel (20% ethyl acetate in hexane) afforded 0.5 g of material containing the thione, which was again purified by flash chromatography (5% ethyl acetate-hexane) to yield 280 mg (26.4%) of 2-phenyl-3,5,6-triethyl-4(3H)-pyrimidinthione (compound 124), as an oil. $^1$H-NMR (CDCl$_3$) δ1.25 (9H, m); 2.7 (2H, q); 3.05 (2H, q); 4.6 (2H, q); 7.5 (5H, m).

Method Z11—Preparation of 5,6-Diethyl-2-phenyl-3-(3-trimethylsilylprop2-ynyl)-4(3H)-pyrimidinone (Compound 182)

To an oven-dried 50 mL 3-neck flask were charged 0.9 g (3.38 mmol) of 5,6-diethyl-2-phenyl-3-propargyl-4(3H)-pyrimidinone and 25 mL freshly distilled THF. The solution was cooled to −70° C. and 2.2 mL of 1.6M (3.52 mmol) n-butyllithium in hexane was added at a rate to maintain the temperature below −62 C. during the addition. The reaction mixture turned black and was allowed to stir for 12 minutes at −70° C. A 0.47 mL (3.70 mmol) portion of trimethylsilyl chloride was added and the reaction stirred for 20 minutes at −70° C. The dry ice bath was removed and the reaction was left to stir and warm to room temperature overnight. The THF was removed in vacuo and ether was added. The ether solution was washed 3 times with water then dried over MgSO$_4$ and concentrated to yield 1.2 g of crude product, as a brown oil. The crude product was purified by chromatography on a 30 g silica gel column eluting with 18% ethyl acetate in hexane. 0.8 g (70% yield) of 5,6-diethyl-2-phenyl-3-(3-trimethylsilyl-2-propynyl)-4(3H)-pyrimidinone (compound 182), was obtained as a yellow oil. $^1$H-NMR (CDCl$_3$) 0.18(9H,s), 1.25(6H,m), 2.65(4H,q), 4.6(2H,s), 7.6(3H,m), 7.42–7.8(5H,m)

Method Z12—Preparation of 5-ethyl-3-(pent-2-yn-4-en-1-yl)-2-phenyl-6-trifluoromethyl-4(3H)-pyrimidinone (Compound 111)

To a deoxygenated solution of 1.01 g (3.28 mmol) of 5-ethyl-2-phenyl-3-propargyl-6-trifluoromethyl-4(3H)-pyrimidinone and 0.61 g (3.96 mmol) of vinyl iodide in 25 mL of triethylamine was added a mixture of 60 mg of copper (I) iodide and 60 mg of bis(triphenylphosphine) palladium (II) chloride. The mixture was stirred at room temperature for 22 h and rotovapped to remove the bulk of the triethylamine. The residue was taken up in 150 mL of ethyl acetate, washed with 75 mL of 5% aqueous hydrochloric acid, 75 mL of saturated aqueous sodium bicarbonate and 75 mL of brine, and dried. Removal of the solvent left 1.51 g of a brown tar. Flash chromatography on a column of 30 g of silica gel eluting with 20, 40, 60 and 60% ether in hexanes afforded 0.31 g of crude 5-ethyl-3-(pent-2-yn-4-en-1-yl)-2-phenyl-6-trifluoromethyl-4(3H)-pyrimidinone. A second chromatography yielded 0.25 g (23%) of pure 5-ethyl-3-(pent-2-yn-4-en-1-yl)-2-phenyl-6-trifluoromethyl-4(3H)-pyrimidinone (compound 111) as a solid, mp 104°-106° C. $^1$H-NMR (CDCl$_3$) d 1.25(3H,t), 2.8(2H,q), 4.75(2H,s), 5.5-5.9(3H,m), 7.55(3H,m), 7.7(2H,m).

Z13—Preparation of 2-(1-methyl-3-pyridinium)-5-ethyl-3-propargyl-6-trifluoromethyl-4(3H)-pyrimidinone iodide (Compound 61)

A solution of 1.23 g (4.01 mmol) of 5-ethyl-3-propargyl-2-(3-pyridyl)-6-trifluoromethyl-4(3H)-pyrimidinone and 1.0 mL (16.1 mmol) of methyl iodide in 5 mL of CHCl$_3$ was heated at reflux for 6 h. An additional 1.0 mL portion of methyl iodide was added and refluxing was continued overnight. The mixture was rotovapped to leave 1.86 g of 2-(1-methyl-3-pyridinium)-5-ethyl-3-propargyl-6-trifluoromethyl-4(3H)-pyrimidinone iodide as a brown solid. $^1$H-NMR (CDCl$_3$) δ1.2(3H,t), 2.7(1H,t), 2.75(2H,q), 4.65(3H,s), 4.9(2H,d), 8.4(1H,t), 8.9(1H,d), 9.2(1H,s), 9.5(1H,d).

Method Z14—Preparation of 5,6-diethyl-2-(3-formylphenyl)-3-propargyl-4(3H)-pyrimidinone (Compound 69)

To a solution of 2.3 g (6.8 mmol) of 5,6-diethyl-2-[3-(2-dioxolanyl)phenyl]-3-propargyl-4(3H)-pyrimidinone in 1 mL of ethyl acetate was added 50 mL of 6M hydrochloric acid and the mixture was stirred for 4 hours. The reaction was followed by gas chromatography and TLC(20% ethyl acetate in hexane). Upon completion of reaction, 75 mL of ether and 150 mL of water were added to the reaction mixture. The layers were separated and the aqueous layer was extracted twice with 50 mL of ether. The organic layers were combined, dried over MgSO$_4$ and concentrated to yield 1.73 g of 5,6-diethyl-2-(3-formylphenyl)-3-propargyl-4(3H)-pyrimidinone (Compound 69) as a yellow oil (86%), which solidified on standing. Mp.=82°-86° C. $^1$H-NMR (CDCl$_3$) δ1.25(6H,m), 2.4(1H,t), 2.65(4H,q), 4.6(2H,d), 7.7(1H,t), 8.05(2H,m), 8.25(1H,s), 10.15(1H,s).

Method Z15—Preparation of 3,6-diethyl-2-phenyl-5-trifluoromethyl-4(3H)-pyrimidinone (Compound 185)

A mixture of 1.00 g (2.8 mmol) of 3,6-diethyl-5-iodo-2-phenyl-4(3H)-pyrimidinone, 1.08 g (5.7 mmol) of copper (I) iodide, 1.54 g (11.3 mmol) of sodium trifluoroacetate and 8 mL of anhydrous N-methylpyrrolidinone was heated at 175 C. for 2 h. The mixture was cooled, diluted with 175 mL of ether, washed with four 50 mL portions of water and dried over MgSO$_4$. Removal of the solvent on the rotovap afforded 0.92 g of crude product as a brown oil. This material was purified by flash chromatography on a 25 g column of silica gel eluting with 100 mL portions of 0, 10, 20, 30, 40, 50 and 75% ether in hexanes to afford 0.35 g of 3,6-diethyl-2-phenyl-5-trifluoromethyl-4(3H)-pyrimidinone (compound 185) as a white solid. $^1$H-NMR (CDCl$_3$) 1.25(3H,t), 1.30(3H,t), 2.8(2H,q), 4.0(2H,q), 7.5(5H).

Method Z16—Preparation of 5,6-Diethyl-2-(3-hydroxyiminophenyl)-3-propargyl-4(3H)-pyrimidinone (Compound 139)

To a 100 mL RBF were charged 1.1 g (3.7 mmol) of 5,6-diethyl-2-(3-formyl-phenyl)-3-propargyl-4(3H)-pyrimidinone, 0.52 g (7.5 mmol) of hydroxylamine hydrochloride and 50 mL of ethanol. The reaction mixture was refluxed for 17 hours. The ethanol was removed in vacuo and ether and ethyl acetate were added to the residue. The organics were washed 3 times with water. The organic layer was gravity filtered to remove 0.22 g of 5,6-diethyl-2-(3-hydroxyiminophenyl)-3-propargyl-4(3H)-pyrimidinone (compound 139). The organic layer was dried over MgSO$_4$ and concentrated to yield a further 0.67 g of 5,6-diethyl-2-(3-hydroxyiminophenyl)-3-propargyl-4(3H)-pyrimidinone (compound 139) as a white solid. A combined yield of 77.6% was obtained. $^1$H-NMR (CDCl$_3$) 1.25(6H,m); 2.35(1H,t); 2.65(4H,m); 4.6(2H,d); 7.49-8.15(4H,m); 8.7(1H,s)

Method Z17—Preparation of 5,6-Diethyl-2-(3-cyanophenyl)-3-propargyl-4(3H)-pyrimidinone (Compound 137)

To an ice cooled solution of 0.64 g (2.07 mmol) of 5,6-diethyl-2-(3-hydroxyiminophenyl)-3-propargyl-4(3H)-pyrimidinone in 10 mL methylene chloride, 1.5 mL (20.5 mmol) of thionyl chloride was added dropwise. The ice bath was removed and the reaction continued to stir at room temperature for 16 h. The reaction mixture was concentrated and 10 mL portions of methylene chloride were added and removed in vacuo twice. 0.65 g of a light brown solid was obtained as crude product. This was combined with 0.15 g crude product from a previous run. The crude product was purified by passing it through a 4 inch plug of basic alumina and washing with 700 mL of methylene chloride. 400 mg of 5,6-diethyl-2-(3-cyanophenyl)-3-propargyl-4(3H)-pyrimidinone (compound 137) was obtained. $^1$H-NMR (CDCl$_3$) 1.25(6H,m); 2.4(1H,t); 2.65(4H,m); 4.58(2H,d); 7.64-8.1(4H,m).

Method Z18—Preparation of 5-ethyl-3-(3-iodopropargyl)-2-phenyl-6-trifluoromethyl-4(3H)-pyrimidinone (Compound 219)

A stirred solution of 1.53 g (5.0 mmol) of 5-ethyl-2-phenyl-3-propargyl-6-trifluoromethyl-4(3H)-pyrimidinone (Compound 46) in 30 mL of THF was cooled to −70° C. and 4.5 mL of 1.6M n-BuLi in hexanes (7.2 mmol) was added dropwise over 15 min. The mixture was stirred at −70° C. for 45 min and a solution of 1.50 g (6.7 mmol) of N-iodosuccinimide in 10 mL of THF was added dropwise over 15 min. The mixture was stirred at −70° C. for 45 min and at room temperature for 30 min. The mixture was diluted with 175 mL of ether, washed with two 50 mL portions of water and 50 mL of saturated aqueous NaHCO$_3$ and dried over MgSO$_4$. Removal of the solvent left 2.36 g of crude product as a brown solid which was purified by flash chromatography on 30 g of silica gel, eluting with 0, 10, 20, 30 and 40% ether in hexanes, to furnish 0.96 g (44%) of 5-ethyl-3-(3-iodopropargyl)-2-phenyl-6-trifluoromethyl-4(3H)-pyrimidinone (Compound 219) as a an off-white solid, m.p. 120°-125° C. (dec). $^1$H-NMR (CDCl$_3$) δ1.25(3H,t), 2.75(2H,q), 4.75(2H,s), 7.5-7.7(5H).

METHODS OF USE

In another aspect, this invention relates to a method of controlling weeds comprising applying to said weed or the locus of said weed or to the surface of the growth medium of said weed a herbicidally effective amount of a compound of the formula:

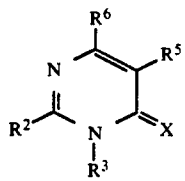

Ia wherein $R^2$ is a substituted or unsubstituted aryl group (e.g. aromatic ring structure having four to ten carbon atoms) or a substituted or unsubstituted heteroaromatic group (e.g. a heteroaromatic ring structure having four to five carbon atoms and one heteroatom selected from nitrogen, oxygen or sulfur); $R^3$ is an alkyl, haloalkyl, polyhaloalkyl, alkenyl, haloalkenyl, polyhaloalkenyl, alkynyl, haloakynyl, polyhaloalkynyl, alkenynyl, alkoxyalkyl, dialkoxyalkyl, haloalkoxyalkyl, oxoalkyl, trimethylsilylalkynyl, cyanoalkyl or aryl group; $R^5$ is a hydrogen, halogen, alkyl, alkenyl, alkynyl, alkoxy, alkylthio, alkoxycarbonylalkyl, haloalkyl, haloalkenyl, haloalkynyl, haloalkoxy, polyhaloalkyl, polyhaloalkenyl, polyhaloalkynyl, polyhaloalkoxy, trimethylsilylalkynyl, or cyano group; and $R^6$ is a hydrogen, halo, alkyl, alkenyl, alkynyl, alkoxy, haloalkoxy, alkylthio, haloalkylthio, alkoxyalkyl, alkoxycarbonyl, alkoxycarbonylalkyl, haloalkyl, haloalkenyl, haloalkynyl, polyhaloalkyl, polyhaloalkenyl, polyhaloalkynyl, polyhaloalkoxy, polyhaloalkythio, cycloalkyl, aryl, heterocyclyl, aralkyl, aryloxy, alkylamino, dialkylamino, dialkylaminocarbonyl, or cyano group; the aryl, aralkyl and aryloxy groups may be substituted or unsubstituted; and X is oxygen or sulfur. The particulars as to the substituents and preferences therefore are the same as stated hereinabove in the compound embodiments. Such herbicidal compositions additionally can comprise one or more carriers suitable for herbicidal compositions.

The compounds of the invention are useful as preemergence and postemergence herbicides. In general, they require lower doses to control weeds preemergence. Preemergence herbicides are usually applied to the soil either before, during or after seeding, but before the crop emerges. Postemergence herbicides are applied after the plants have emerged and during their growth period. The embodied materials generally show selectivity to several agronomically important crops such as corn, cotton, rice, soybean, sugarbeet, sunflower, peanut and wheat.

Under some conditions the compounds of the invention may be incorporated into the soil or other growth medium prior to planting a crop. This incorporation may be by any convenient means, including mixing with the soil, applying the compound to the surface of the soil and then dishing or dragging into the soil to the desired depth, or by employing a liquid carrier.

The 2-arylpyrimidines of the present invention can be applied to various loci such as the soil or the foliage. For such purposes these compounds can be used in the technical or pure form as prepared, as solutions or as formulations. The compounds are usually taken up in a carrier or are formulated so as to render them suitable for subsequent dissemination as herbicides. For example, these chemical agents can be formulated as wettable powders, emulsifiable concentrates, dusts, granular formulations, aerosols, or flowable emulsion concentrates. In such formulations, the compounds are extended with a liquid or solid carrier and, when desired, suitable surfactants are incorporated.

It is usually desirable, particularly in the case of foliar spray formulations, to include adjuvants, such as wetting agents, spreading agents, dispersing agents, stickers, adhesive and the like in accordance with agricultural practices. Such adjuvants commonly used in the art can be found in the John W. McCutcheon, Inc. publication "Detergents and Emulsifiers, Annual." Allured Publishing Company, Ridgewood, N.J., U.S.A.

The 2-arylpyrimidines can be applied as herbicidal sprays by methods commonly employed, such as conventional high-gallonage hydraulic sprays, low-gallonage sprays, air-blast spray, aerial sprays and dusts. The dilution and rate of application will depend upon the type of equipment employed, the method of application and weeds to be controlled, but the preferred effective amount is usually from about 0.01 lb. to about 10 lbs. per acre to the active ingredient.

As a soil treatment the chemical can be incorporated in the soil or applied to the surface usually at a rate of from about 0.01 to about 10 lbs. per acre. As a foliar spray, the toxicant is usually applied to growing plants at a rate of from about 0.01 to about 10 lbs. per acre.

The 2-arylpyrimidines of the invention can also be mixed with fertilizers or fertilizing materials before their application. In one type of solid fertilizing composition in which the arylpyrimidines can be used, particles of a fertilizer or fertilizing ingredients, such as ammonium sulfate, ammonium nitrate, or ammonium phosphate, can be coated with one or more of the compounds. The solid compounds and solid fertilizing material can also be admixed in mixing or blending equipment, or they can be incorporated with fertilizers in granular formulations. Any relative proportion of fertilizer can be used which is suitable for the crops and weeds to be treated. The 2-arylpyrimidine will commonly be from about 5% to about 25% of the fertilizing composition. These compositions provide fertilizing materials which promote the rapid growth of desired plants, and at the same time control the growth of undesired plants.

For some applications, one or more other herbicides may be added of the herbicides of the present invention, thereby providing additional advantages and effectiveness. When mixtures of herbicides are employed, the relative proportions which are used will depend upon the relative efficacy of compounds in the mixture with respect to the plants to be treated. Examples of other herbicides which can be combined with those of the present invention include:

CARBOXYLIC ACIDS AND DERIVATIVES 2,3,6-trichlorobenzoic acid and its salts;
2,3,5,6-tetrachlorobenzoic acid and its salts;
2-methoxy-3,5,6-trichlorobenzoic acid and its salts;
2-methoxy-3,6-dichlorobenzoic acid and its salts;
2-methyl-3,6-dichlorobenzoic acid and its salts;
2,3-dichloro-6-methylbenzoic acid and its salts;
2,4-dichlorophenoxyacetic acid and its salts and esters;
2,4,5-trichlorophenoxyacetic acid and its salts and esters;
2-methyl-4-chlorophenoxyacetic acid and its salts and esters;
2-(2,4,5-trichlorophenoxy)propionic acid and its salts and esters;
4-(2,4-dichlorophenoxy)butyric acid and its salts and esters;

4-(2-methyl-4-chlorophenoxy)butyric acid and its salts
and esters;
2,3,6-trichlorophenylacetic acid and its salts;
3,6-endoxohexahydrophthalic acid and its salts;
dimethyl 2,3,5,6-tetrachloroterephthalate; trichloroacetic acid and its salts;
2,2-dichloropropionic acid and its salts;
2,3-dichloroisobutyric acid and its salts;
isopropylammonium 2-(4-isopropyl-4-methyl-5-oxo-2-imidazolin-2-yl)nicotinate;
2-[4,5-dihydro-4-methyl-4-(1-methylethyl)-5-oxo-1H-imidazol-2-yl]-3-quinolinecarboxylic acid;
6-(4-isopropyl-4-methyl-5-oxo-2-imidazolin-2-yl)-m-toluic acid, methyl ester and
6-(4-isopropyl-4-methyl-5-oxo-2-imidazolin-2-yl)-p-toluic acid, methyl ester;
N-(phosphomethyl)glycine isopropylammonium salt;
[3,5,6-trichloro-(2-pyridinyl)oxy]acetic acid;
3,7-dichloro-8-quinolinecarboxylic acid;
ammonium DL-homoalanin-4-yl(methyl)phosphinate;

CARBAMIC ACID DERIVATIVES ethyl N,N-di(n-propyl)thiolcarbamate;
n-propyl N,N-di(n-propyl)thiolcarbamate;
ethyl N-ethyl-N-(n-butyl)thiolcarbamate;
n-propyl N-ethyl-N-(n-butyl)thiolcarbamate;
2-chloroallyl N,N-diethyldithiocarbamate;
isopropyl N-phenylcarbamate;
isopropyl N-(m-chlorophenyl)carbamate;
4-chloro-2-butynyl-N-(m-chlorophenyl)carbamate;
methyl N-(3,4-dichlorophenyl)carbamate;
dinitro-o-(sec-butyl)phenol and its salts;
pentachlorophenol and its salts
S-(4-chlorobenzyl)-N,N-diethylthiolcarbamate;

SUBSTITUTED UREAS 2-chloro-N-[(4-methoxy-6-methyl-1,3,5-triazin-2-yl)aminocarbonyl]-benzenesulfonamide;
3-(3,4-dichlorophenyl)-1,1-dimethylurea;
3-phenyl-1,1-dimethylurea;
3-(3,4-dichlorophenyl)-3-methoxy-1,1-dimethylurea;
3-(4-chlorophenyl)-3-methoxy-1,1-dimethylurea;
3-(3,4-dichlorophenyl)-1-n-butyl-1-methylurea;
3-(3,4-dichlorophenyl)-1-methoxy-1-methylurea;
3-(4-chlorophenyl)-1-methoxy-1-methylurea;
3-(3,4-dichlorophenyl)-1,1,3-trimethylurea;
3-(3,4-dichlorophenyl)diethylurea;
N-(4-isopropylphenyl)-N,N'-dimethylurea;
dichloral urea;
methyl 2-[[[[(4,6-dimethyl-2-pyrimidinyl)amino]-carbonyl]amino]sulfonyl]benzoate;
N-((6-methoxy-4-methyl-1,3,5-triazin-2-yl)aminocarbonyl)-2-(2-chloroethoxy)benzenesulfonamide;
2-[[[(4-chloro-6-methoxypyrimidine-2-yl)aminocarbonyl]amino]sulfonyl]benzoic acid, ethyl ester;
methyl 2-[[[[(4-methoxy-6-methyl-1,3,5-triazin-2-yl)amino]-carbonyl]amino]-sulfonyl]benzoate;
methyl 3-[[(4-methoxy-6-methyl-1,3,5-triazin-2-yl)aminocarbonyl]aminosulfonyl]-2-thio-phenecarboxylate;
methyl 2-[[[[[(4,6-dimethoxypyrimidin-2-yl)amino]carbonyl]amino]sulfonyl]methyl]benzoate;
methyl 2-[[[[(4-methoxy-6-methyl-1,3,5-triazin-2-yl)methylamino]carbonyl]amino]sulfonyl]benzoate;

SUBSTITUTED TRIAZINES 2-chloro-4,6-bis(ethylamino)-s-triazine;
2-chloro-4-ethylamino-6-isopropylamino-s-triazine;
2-chloro-4,6-bis(3-methoxy-n-propylamino)-s-triazine;
2-methoxy-4,6-bis(isopropylamino)-s-triazine;
2-chloro-4-ethylamino-6-(3-methoxy-n-propylamino)-s-triazine;
2-methylmercapto-4,6-bis(isopropylamino)-s-triazine;
2-methylmercapto-4,6-bis(ethylamino)-2-triazine;
2-methylmercapto-4-ethylamino-6-isopropylamino-s-triazine;
2-chloro-4,6-bis(isopropylamino)-s-triazine;
2-methoxy-4-ethylamino-6-isopropylamino-s-triazine;
2-methylmercapto-4-(2-methoxyethylamino)-6-isopropylamino-s-triazine;
4-amino-6-(t-butyl)-3-(methylthio)-1,2,4-triazine-5(4H)-one;

DIPHENYL ETHER DERIVATIVES 2,4-dichloro-4'-nitrodiphenyl ether;
2,4,6-trichloro-4'-nitrodiphenyl ether;
2,4-dichloro-6-fluoro-4'-nitrodiphenyl ether;
3-methyl-4'-nitrodiphenyl ether;
3,5-dimethyl-5'-nitrodiphenyl ether;
2,4'-dinitro-4-(trifluoromethyl)diphenyl ether;
2,4-dichloro-3'-methoxy-4'-nitrodiphenyl ether;
sodium 5-(2-chloro-4-(trifluoromethyl)phenoxy)-2-nitrobenzoate;
2-chloro-1-(3-ethoxy-4-nitrophenoxy)-4-(trifluoromethyl)benzene;
1-(carboethoxy)ethyl 5-[2-chloro-4-(trifluoromethyl)phenoxy]-2-nitrobenzoate;
5-[2-chloro-4-(trifluoromethyl)phenoxyl]-N-(methylsulphony)-2-nitrobenzamide;

ANILIDES 2-chloro-N-(2-ethyl-6-methylphenyl)-N-(2-methoxy-1-methylethyl)acetamide;
2-chloro-2',6'-diethyl-N-(2-propyloxyethyl)acetanilide;
N-(3,4-dichlorophenyl)propionamide;
N-(3,4-dichlorophenyl)methacrylamide;
N-(3-chloro-4-methylphenyl)-2-methylpentanamide;
N-(3,4-dichlorophenyl)trimethylacetamide;
N-(3,4-dichlorophenyl)-alpha,alpha-dimethylvaleramide;
N-isopropyl-N-phenylchloroacetamide;
N-n-butoxymethyl-N-(2,6-diethylphenyl)chloroacetamide;
N-methoxymethyl-N-(2,6-diethylphenyl)chloroacetamide;

OXYPHENOXY HERBICIDES 2-(4-(2,4-dichlorophenoxy)phenoxy)methyl propionate;
methyl 2-(4-(3-chloro-5-(trifluoromethyl)-2-pyridinyloxy)phenoxy)propanoate;
butyl (R)-2-[4-[5-(trifluoromethyl)-2-pyridinyloxy]-phenoxy]propionate;
ethyl 2-[4-[(6-chloro-2-benzoxazolyl)oxy]phenoxy]propanoate;
butyl 2-[4-[[5-(trifluoromethyl)-2-pyridinyl]oxy]-phenoxy]propionate;
2-[4-[(6-chloro-2-quinoxalinyl)oxy]phenoxy]propionic acid, ethyl ester;

URACILS 5-bromo-3-s-butyl-6-methyluracil;
5-bromo-3-cyclohexyl-1,6-dimethyluracil;
3-cyclohexyl-5,6-trimethyleneuracil;
5-bromo-3-isopropyl-6-methyluracil;
3-tert-butyl-5-chloro-6-methyluracil;

NITRILES 2,6-dichlorobenzonitrile;
diphenylacetonitrile;
3,5-dibromo-4-hydroxybenzonitrile;
3,5-diiodo-4-hydroxybenzonitrile;

OTHER ORGANIC HERBICIDES 2-chloro-N,N-diallylacetamide;
N-(1,1-dimethyl-2-propynyl)-3,5-dichlorobenzamide;
maleic hydrazide;
3-amino-1,2,4-triazole; monosodium methanearsonate; disodium methanearsonate;
N,N-dimethyl-alpha,alpha-diphenylacetamide;
N-N-di(n-propyl)-2,6-dinitro-4-(trifluoromethyl)aniline;
N,N-di(n-propyl)-2,6-dinitro-4-methylaniline;
N,N-di(n-propyl)-2,6-dinitro-4-methylsulfonylaniline;
O-(2,4-dichlorophenyl)-O-methyl isopropylphosphoramidothioate;
4-amino-3,5,6-trichloropicolinic acid;
2,3-dichloro-1,4-naphthoquinone;
di(methoxythiocarbonyl)disulfide;
3-(1-methylethyl)-1H-2,1,3-benzothiadiazin-(4)3H-one-2,2-dioxide;
6,7-dihydrodipyridol[1,2-a:2',1'-c]pyrazidiium salts;
1,1'-dimethyl-4,4'-bipyridinium salts;
3,4,5,6-tetrahydro-3,5-dimethyl-2-thio-2H-1,3,5-thiadiazine;
2-[1-(ethoxyimino)butyl]-5-[s-(ethylthio)propyl]-3-hydroxy-2-cyclohexen-1-one;
2-(2-chlorophenyl)methyl-4,4-dimethyl-3-isoxazolidinone;
N-(1-ethylpropyl)-3,4-dimethyl-2,6-dinitrobenzamide;
4-chloro-5-(methylamino)-2-(a,a,a-trifluoro-m-toluyl)-3-(2H)-pyridazinone;
2-(3,5-dichlorophenyl)-2-(2,2,2-trichloromethyl)oxirane.

When mixtures of herbicides are employed, the relative proportions which are used will depend upon the crop to be treated and the degree of selectivity in weed control desired. The herbicidal activity of the 2-arylpyrimidines of the present invention towards a number of common weeds was evaluated using a greenhouse method of testing. Using the procedures described below, the aryl pyrimidines of the present invention were evaluated for control of weeds selected from the following:

| Monocots | |
|---|---|
| Barnyardgrass (BYG) | Echinochloa crus-galli |
| Crabgrass (CRB) | Digitaria sanguinilis |
| Foxtail (FOX) | Setaria viridis |
| Johnsongrass (JON) | Sorghum halepense |
| Meadow Foxtail (MF) | Alopecurus pratensis |
| Nutsedge (NUT) | Cyperus esculentus |
| Wild Oat (WO) | Avena fatua |
| Dicots | |
| Beggartick (BID) | Bidens pilosa |
| Cocklebur (CKL) | Xanthium strumarium |
| Morningglory (MG) | Ipomoea Lacunosa |
| Nightshade (NS) | Solanum nigrum |
| Pigweed (PIG) | Amaranthus retroflexus |
| Smartweed (SMT) | Polygonum lapathifolium |
| Velvetleaf (VEL) | Abutilon theophrasti |

The following test procedure was employed. Seeds of selected plants were planted in flats or pots. For pre-emergence tests, immediately after planting, the test compound was sprayed directly onto the soil surface. The flats or pots were placed in the greenhouse and then watered. For postemergence tests, the seeds were allowed to germinate and grow for 10 to 21 days. Before application, each series of test plants were selected for uniformity, size and stage of development. The test plants were then treated with the test compound, returned to the greenhouse and watered.

The compound to be evaluated was dissolved in an appropriate solvent, usually acetone, and sprayed over the flats or pots using a carrier volume equivalent to 25 or 50 gallons per acre at the rate of application in pounds per acre (Lb/A) or grams per hectare (g/Ha) specified in the below tables. About two or three weeks after application of the test compound, the state of growth of the plant was observed. Each species was evaluated on a scale of 0–100 in which 0 equals no activity and 100 equals total control. The column heading abbreviations in the below tables for the plants tested are the same as for the monocots and dicots hereinabove. The dash ("-") entry signifies no testing for the specified conditions. The following tables show the results obtained for the test compounds at the stated rate of application and are provided merely as illustrations and are not to be considered as limitations or restrictions of the scope of this invention which is defined by the claims.

TABLE 3

| COMPOUND | TYPE | LB/A | CKL | MG | PIG | SMT | VEL | BYG | FOX | JON | NUT | WO |
|---|---|---|---|---|---|---|---|---|---|---|---|---|
| 1 | PRE | 4.00 | 20 | 100 | 100 | 100 | 100 | 100 | 100 | 99 | 55 | 100 |
|   | POST | 4.00 | 25 | 70 | 100 | 100 | 55 | 80 | 50 | 0 | 15 | 100 |
| 2 | PRE | 4.00 | 5 | 100 | 100 | 100 | 100 | 100 | 100 | 100 | 65 | 60 |
|   | POST | 4.00 | 15 | 75 | 75 | 50 | 35 | 80 | 75 | 0 | 0 | 35 |
| 4 | PRE | 4.00 | 25 | 100 | 100 | 100 | 100 | 100 | 100 | 100 | 85 | 100 |
|   | POST | 4.00 | 20 | 45 | 100 | 55 | 50 | 95 | 95 | 70 | 35 | 90 |
| 5 | PRE | 4.00 | 40 | 100 | 100 | 100 | 100 | 100 | 100 | 100 | 100 | 98 |
|   | POST | 4.00 | 20 | 85 | 70 | 99 | 65 | 98 | 95 | 65 | 80 | 70 |
| 6 | PRE | 4.00 | 15 | 100 | 100 | 100 | 100 | 100 | 100 | 100 | 100 | 85 |
|   | POST | 4.00 | 0 | 10 | 45 | 40 | 0 | 20 | 0 | 70 | 15 | 0 |
| 7 | PRE | 4.00 | 0 | 10 | — | 100 | 60 | 90 | 100 | 55 | — | 40 |
|   | POST | 4.00 | 0 | 0 | 20 | 15 | 20 | 0 | 0 | 0 | 0 | 0 |

"—" EQUALS NOT TESTED

TABLE 3A

| COMPOUND | TYPE | LB/A | BID | NS | SMT | VEL | BYG | CRB | FOX | MF |
|---|---|---|---|---|---|---|---|---|---|---|
| 8 | PRE | 4.00 | 100 | 100 | 100 | 100 | 100 | 100 | 100 | — |
|   | POST | 4.00 | 15 | 100 | 5 | 5 | 20 | 20 | 75 | 65 |
| 9 | PRE | 2.00 | — | 80 | 100 | 10 | 100 | — | 100 | — |

TABLE 3A-continued

| COMPOUND | TYPE | LB/A | BID | NS | SMT | VEL | BYG | CRB | FOX | MF |
|---|---|---|---|---|---|---|---|---|---|---|
|    | POST | 2.00 | — | 30 | 0 | 0 | 0 | — | 0 | — |
| 11 | PRE  | 2.00 | — | 100 | 100 | 100 | 100 | — | 100 | — |
|    | POST | 2.00 | — | 45 | 0 | 0 | 15 | — | 15 | — |
| 12 | PRE  | 1.00 | 25 | 100 | 100 | 100 | 100 | 100 | 100 | 100 |
|    | POST | 1.00 | 25 | 100 | 100 | 35 | 95 | 95 | 95 | 95 |
| 13 | PRE  | 1.00 | 0 | 100 | 95 | 0 | 90 | 100 | 100 | 90 |
|    | POST | 1.00 | 0 | 20 | 20 | 20 | 0 | 20 | 0 | 0 |
| 14 | PRE  | 1.00 | 60 | 100 | 100 | 95 | 100 | 100 | 100 | 100 |
|    | POST | 1.00 | 75 | 95 | 95 | 80 | 100 | 95 | 80 | 50 |
| 15 | PRE  | 1.00 | 25 | 40 | 100 | 90 | 0 | 80 | 0 | 0 |
|    | POST | 1.00 | 0 | 60 | 0 | 0 | 0 | 0 | 0 | 0 |
| 16 | PRE  | 1.00 | 80 | 100 | 100 | 90 | 95 | 85 | 90 |    |
|    | POST | 1.00 | 35 | 100 | 95 | 10 | 90 | 95 | 85 | 90 |
| 17 | PRE  | 1.00 | 0 | 90 | 100 | 80 | 40 | 90 | 25 | 0 |
|    | POST | 1.00 | 20 | 100 | 20 | 0 | 0 | 20 | 0 | 0 |
| 18 | PRE  | 1.00 | 0 | 0 | 0 | 0 | 0 | 40 | 0 | 0 |
|    | POST | 1.00 | 0 | 100 | 0 | 0 | 0 | 0 | 0 | 0 |
| 19 | PRE  | 1.00 | 0 | 25 | 25 | 0 | 0 | 0 | 0 | 0 |
|    | POST | 1.00 | 10 | 100 | 0 | 20 | 0 | 0 | 0 | 0 |
| 20 | PRE  | 1.00 | 50 | 75 | 20 | 40 | 75 | 90 | 100 | 75 |
|    | POST | 1.00 | 0 | 0 | 0 | 0 | 0 | 0 | 0 | 0 |
| 21 | PRE  | 1.00 | 0 | 10 | 90 | 0 | 90 | 100 | 50 | 90 |
|    | POST | 1.00 | 0 | — | 0 | 0 | 0 | 0 | 0 | 0 |
| 22 | PRE  | 1.00 | 90 | 100 | 100 | 100 | 100 | 100 | 100 | 100 |
|    | POST | 1.00 | 70 | — | 100 | 0 | 100 | 100 | 80 | 100 |
| 23 | PRE  | 1.00 | 25 | 95 | 0 | 100 | 25 | 0 | 95 | 100 |
|    | POST | 1.00 | 10 | — | 10 | 0 | 0 | 20 | 0 | 0 |
| 25 | PRE  | 1.00 | 0 | — | 0 | 0 | 0 | 0 | 0 | 0 |
|    | POST | 1.00 | 25 | 50 | 25 | 0 | 0 | 0 | 0 | 0 |
| 26 | PRE  | 1.00 | 0 | — | 0 | 0 | 50 | 75 | 40 | 0 |
|    | POST | 1.00 | 0 | 0 | 0 | 0 | 0 | 0 | 0 | 0 |
| 27 | PRE  | 1.00 | 0 | — | — | 20 | 95 | 100 | 100 | 100 |
|    | POST | 1.00 | 0 | 85 | 60 | 0 | 75 | 75 | 10 | 75 |
| 28 | PRE  | 1.00 | 0 | — | — | 20 | 100 | 100 | 100 | 100 |
|    | POST | 1.00 | 20 | 95 | 50 | 60 | 95 | 95 | 50 | 90 |
| 29 | PRE  | 1.00 | 25 | — | — | 60 | 100 | 100 | 100 | 100 |
|    | POST | 1.00 | 25 | 100 | 100 | 50 | 95 | 95 | 90 | 100 |
| 30 | PRE  | 1.00 | 0 | 0 | 25 | 0 | 60 | 100 | 90 | 80 |
|    | POST | 1.00 | 0 | 75 | 0 | 0 | 0 | 0 | 0 | 0 |
| 31 | PRE  | 1.00 | 10 | 100 | 100 | 20 | 100 | 100 | 100 | 100 |
|    | POST | 1.00 | 25 | 90 | 95 | 20 | 95 | 100 | 70 | 95 |
| 32 | PRE  | 1.00 | 0 | 95 | 100 | 25 | 95 | 100 | 100 | 95 |
|    | POST | 1.00 | 25 | 90 | 90 | 20 | 95 | 95 | 80 | 90 |
| 33 | PRE  | 1.00 | 20 | 100 | 100 | 0 | 95 | 100 | 100 | 100 |
|    | POST | 1.00 | 20 | 80 | 40 | 0 | 25 | 25 | 25 | 50 |
| 35 | PRE  | 1.00 | 20 | 0 | 100 | 40 | 100 | 100 | 100 | 100 |
|    | POST | 1.00 | 10 | 95 | 95 | 10 | 95 | 95 | 70 | 60 |
| 36 | PRE  | 1.00 | 0 | 100 | 60 | 0 | 75 | 95 | 75 | 75 |
|    | POST | 1.00 | 40 | 80 | 40 | 0 | 50 | 40 | 40 | 10 |
| 37 | PRE  | 1.00 | 10 | 95 | 95 | 10 | 90 | 95 | 90 | 90 |
|    | POST | 1.00 | 30 | 25 | 40 | 0 | 20 | 0 | 0 | 0 |
| 38 | PRE  | 1.00 | 0 | 25 | 0 | 80 | 0 | 0 | 0 | 0 |
|    | POST | 1.00 | 20 | 20 | 0 | 0 | 0 | 0 | 0 | 0 |
| 39 | PRE  | 1.00 | 80 | 95 | — | 80 | 95 | 100 | 100 | 100 |
|    | POST | 1.00 | 70 | 95 | 90 | 25 | 90 | 95 | 60 | 95 |
| 40 | PRE  | 1.00 | 0 | 90 | — | 0 | 50 | 75 | 80 | 0 |
|    | POST | 1.00 | 40 | 0 | 0 | 0 | 25 | 0 | 0 | 0 |
| 41 | PRE  | 1.00 | 40 | 25 | 100 | 95 | 0 | 60 | 40 | 0 |
|    | POST | 1.00 | 0 | 0 | 0 | 0 | 0 | 0 | 0 | 0 |
| 45 | PRE  | 1.00 | 0 | 95 | 100 | 0 | 85 | 95 | 100 | 95 |
|    | POST | 1.00 | 70 | 90 | 90 | 60 | 85 | 80 | 20 | 85 |
| 46 | PRE  | 1.00 | 80 | 100 | 100 | 100 | 100 | 100 | 100 | 100 |
|    | POST | 1.00 | 95 | 100 | 100 | 85 | 95 | 100 | 95 | 95 |
| 47 | PRE  | 1.00 | 0 | 90 | 90 | 20 | 95 | 95 | 95 | 95 |
|    | POST | 1.00 | 0 | 100 | 0 | 0 | 25 | 25 | 0 | 0 |
| 48 | PRE  | 1.00 | 95 | 100 | 100 | 80 | 100 | 100 | 100 | 100 |
|    | POST | 1.00 | 70 | 100 | 100 | 70 | 100 | 95 | 90 | 95 |
| 51 | PRE  | 1.00 | 80 | 95 | 20 | 50 | 100 | 95 | 100 | 100 |
|    | POST | 1.00 | 20 | 90 | 25 | 0 | 40 | 50 | 20 | 0 |
| 52 | PRE  | 2.00 | — | 95 | 100 | 0 | 35 | — | 100 | — |
|    | POST | 2.00 | — | 0 | 0 | 0 | 0 | — | 0 | — |
| 53 | PRE  | 1.00 | 0 | 90 | — | 25 | 90 | 95 | 95 | 40 |
|    | POST | 1.00 | 0 | 90 | 80 | 10 | 50 | 40 | 25 | 10 |
| 54 | PRE  | 1.00 | 100 | 100 | 95 | 100 | 100 | 100 | 100 | 100 |
|    | POST | 1.00 | 95 | 100 | 100 | 90 | 95 | 95 | 95 | 95 |
| 55 | PRE  | 1.00 | 25 | 95 | 95 | 50 | 100 | 100 | 100 | 100 |
|    | POST | 1.00 | 20 | 90 | 90 | 75 | 80 | 90 | 80 | 80 |
| 56 | PRE  | 1.00 | 95 | 100 | 95 | 40 | 100 | 100 | 100 | 100 |
|    | POST | 1.00 | 70 | 100 | 90 | 50 | 95 | 95 | 95 | 95 |
| 57 | PRE  | 1.00 | 25 | 100 | 85 | 25 | 100 | 100 | 100 | 100 |
|    | POST | 1.00 | 25 | 100 | 90 | 50 | 90 | 95 | 80 | 90 |

TABLE 3A-continued

| COMPOUND | TYPE | LB/A | BID | NS | SMT | VEL | BYG | CRB | FOX | MF |
|---|---|---|---|---|---|---|---|---|---|---|
| 58 | PRE | 1.00 | 95 | 100 | 95 | 100 | 100 | 100 | 100 | 100 |
|  | POST | 1.00 | 80 | 80 | 90 | 85 | 80 | 100 | 75 | 70 |
| 59 | PRE | 1.00 | 20 | 100 | 95 | 80 | 100 | 100 | 100 | 100 |
|  | POST | 1.00 | 20 | 70 | 40 | 20 | 80 | 90 | 40 | 70 |
| 60 | PRE | 1.00 | 40 | 100 | 85 | 40 | 95 | 100 | 100 | 100 |
|  | POST | 1.00 | 25 | 95 | 85 | 25 | 70 | 95 | 60 | 40 |
| 61 | PRE | 1.00 | 0 | 70 | 0 | 0 | 0 | 0 | 0 | 0 |
|  | POST | 1.00 | 0 | 80 | 20 | 0 | 20 | 0 | 20 | 0 |
| 62 | PRE | 1.00 | 90 | 100 | 90 | 100 | 100 | 100 | 100 | 100 |
|  | POST | 1.00 | 80 | 100 | 100 | 90 | 90 | 95 | 95 | 100 |
| 63 | PRE | 1.00 | 0 | 90 | 10 | 0 | 0 | 10 | 20 | 0 |
|  | POST | 1.00 | 10 | 10 | 0 | 0 | 0 | 20 | 0 | 0 |
| 64 | PRE | 1.00 | 20 | 100 | 95 | 50 | 100 | 100 | 100 | 100 |
|  | POST | 1.00 | 60 | 100 | 100 | 75 | 95 | 95 | 95 | 95 |
| 65 | PRE | 1.00 | 10 | 100 | 100 | 20 | 100 | 100 | 100 | 100 |
|  | POST | 1.00 | 40 | 100 | 75 | 50 | 95 | 95 | 95 | 90 |
| 66 | PRE | 1.00 | 10 | 95 | 100 | 100 | 100 | 100 | 100 | 100 |
|  | POST | 1.00 | 70 | 100 | 100 | 80 | 95 | 100 | 90 | 95 |
| 67 | PRE | 1.00 | 0 | 95 | 80 | 10 | 95 | 100 | 100 | 100 |
|  | POST | 1.00 | 10 | 100 | 80 | 20 | 90 | 95 | 90 | 90 |
| 68 | PRE | 1.00 | 50 | 100 | 100 | 40 | 100 | 100 | 100 | 100 |
|  | POST | 1.00 | 70 | 100 | 85 | 70 | 95 | 95 | 85 | 85 |
| 69 | PRE | 1.00 | — | — | 100 | 0 | 0 | 0 | 0 | 0 |
|  | POST | 1.00 | 0 | 50 | 10 | 0 | 0 | 0 | 0 | 0 |
| 70 | PRE | 1.00 | 0 | 100 | 100 | 50 | 100 | 100 | 100 | 100 |
|  | POST | 1.00 | 25 | 80 | 85 | 60 | 70 | 90 | 60 | 50 |
| 71 | PRE | 1.00 | 20 | 100 | 100 | 0 | 100 | 100 | 100 | 100 |
|  | POST | 1.00 | 40 | 95 | 70 | 60 | 80 | 95 | 60 | 70 |
| 76 | PRE | 1.00 | 0 | 100 | 90 | 85 | 95 | 100 | 100 | 100 |
|  | POST | 1.00 | 25 | 100 | 95 | 25 | 85 | 75 | 70 | 75 |
| 77 | PRE | 1.00 | 20 | 100 | 90 | 100 | 100 | 100 | 100 | 100 |
|  | POST | 1.00 | 90 | 100 | 100 | 85 | 95 | 90 | 90 | 90 |
| 79 | PRE | 1.00 | 0 | 0 | 0 | 0 | 0 | 0 | 0 | 0 |
|  | POST | 1.00 | 0 | 50 | 0 | 0 | 0 | 0 | 0 | 0 |
| 80 | PRE | 1.00 | 0 | 90 | 20 | 0 | 60 | 95 | 95 | 70 |
|  | POST | 1.00 | 10 | 95 | 20 | 40 | 0 | 0 | 20 | 0 |
| 81 | PRE | 1.00 | 0 | 0 | 0 | 0 | 0 | 90 | 0 | 0 |
|  | POST | 1.00 | 20 | 20 | 0 | 0 | 0 | 0 | 0 | 0 |
| 83 | PRE | 1.00 | 0 | 90 | 90 | 0 | 70 | 95 | 40 | 30 |
|  | POST | 1.00 | 30 | 50 | 20 | 10 | 0 | 0 | 0 | 0 |
| 84 | PRE | 1.00 | 75 | 95 | 60 | 80 | 90 | 100 | 100 | 100 |
|  | POST | 1.00 | 50 | 100 | 90 | 50 | 85 | 90 | 75 | 75 |
| 85 | PRE | 1.00 | 60 | 80 | 95 | 70 | 100 | 100 | 100 | 100 |
|  | POST | 1.00 | 90 | 100 | 95 | 75 | 95 | 100 | 90 | 90 |
| 87 | PRE | 1.00 | 0 | 0 | 0 | 0 | 80 | 90 | 100 | 90 |
|  | POST | 1.00 | 0 | 20 | 0 | 0 | 25 | 95 | 0 | 0 |
| 88 | PRE | 1.00 | 0 | 90 | 85 | 60 | 95 | 100 | 100 | 95 |
|  | POST | 1.00 | 40 | 100 | 70 | 80 | 85 | 95 | 75 | 80 |
| 89 | PRE | 1.00 | 0 | 0 | 0 | 0 | 0 | 100 | 0 | 0 |
|  | POST | 1.00 | 0 | 70 | 0 | 0 | 0 | 0 | 0 | 0 |
| 90 | PRE | 1.00 | 80 | 100 | 100 | 20 | 100 | 100 | 100 | 100 |
|  | POST | 1.00 | 80 | 100 | 90 | 35 | 95 | 95 | 90 | 90 |
| 91 | PRE | 1.00 | 0 | 0 | 0 | 0 | 10 | 80 | 10 | 0 |
|  | POST | 1.00 | 0 | 0 | 0 | 0 | 0 | 0 | 0 | 0 |
| 92 | PRE | 1.00 | 0 | 0 | 0 | 0 | 0 | 100 | 0 | 0 |
|  | POST | 1.00 | 0 | 0 | 0 | 0 | 0 | 0 | 0 | 0 |
| 94 | PRE | 1.00 | 0 | 100 | 100 | 70 | 100 | — | 100 | 100 |
|  | POST | 1.00 | 70 | 100 | 90 | 60 | 90 | 90 | 85 | 80 |
| 95 | PRE | 1.00 | 60 | 90 | 95 | 70 | 100 | — | 85 | 100 |
|  | POST | 1.00 | 70 | 100 | 85 | 80 | 95 | 90 | 85 | 90 |
| 96 | PRE | 1.00 | 20 | 100 | — | 40 | 90 | 95 | 90 | 95 |
|  | POST | 1.00 | 60 | 100 | 90 | 75 | 95 | 95 | 50 | 90 |
| 97 | PRE | 1.00 | 60 | 100 | — | 25 | 100 | 100 | 100 | 100 |
|  | POST | 1.00 | 85 | 100 | — | 100 | 100 | 100 | 100 | 100 |
| 98 | PRE | 1.00 | 80 | 100 | — | 100 | 100 | 100 | 100 | 100 |
|  | POST | 1.00 | 90 | 100 | 90 | 85 | 95 | 95 | 90 | 90 |
| 99 | PRE | 1.00 | 0 | 100 | 80 | 10 | 100 | 95 | 100 | 100 |
|  | POST | 1.00 | 0 | 100 | 90 | 0 | 80 | 95 | 20 | 90 |
| 103 | PRE | 1.00 | 10 | 95 | 95 | 75 | 100 | 100 | 100 | 100 |
|  | POST | 1.00 | 40 | 95 | 100 | 25 | 100 | 95 | 85 | 95 |
| 105 | PRE | 1.00 | 0 | 0 | 0 | 0 | 0 | 0 | 0 | 0 |
|  | POST | 1.00 | 0 | 25 | 0 | 0 | 0 | 25 | 0 | 0 |
| 106 | PRE | 1.00 | 25 | 90 | 50 | 100 | 100 | — | 100 | 100 |
|  | POST | 1.00 | 50 | 80 | 70 | 60 | 85 | 90 | 70 | 60 |
| 107 | PRE | 1.00 | 95 | 95 | 70 | 50 | 90 | — | 95 | 95 |
|  | POST | 1.00 | 40 | 80 | 85 | 75 | 90 | 85 | 35 | 60 |
| 108 | PRE | 1.00 | 95 | 100 | 95 | 70 | 100 | 100 | 100 | 100 |
|  | POST | 1.00 | 85 | 85 | 80 | 40 | 65 | 90 | 50 | 50 |
| 110 | PRE | 1.00 | 100 | 100 | 100 | 100 | 100 | 100 | 100 | 100 |
|  | POST | 1.00 | 75 | 100 | 85 | 70 | 90 | 95 | 85 | 80 |
| 111 | PRE | 1.00 | 100 | 40 | 20 | 0 | 20 | 100 | 50 | 0 |

TABLE 3A-continued

| COMPOUND | TYPE | LB/A | BID | NS | SMT | VEL | BYG | CRB | FOX | MF |
|---|---|---|---|---|---|---|---|---|---|---|
| | POST | 1.00 | 0 | 60 | 0 | 0 | 10 | 0 | 0 | 0 |
| 112 | PRE | 1.00 | 0 | 100 | 0 | 0 | 80 | — | 95 | — |
| | POST | 1.00 | 0 | 75 | 60 | 35 | 25 | 75 | 15 | 10 |
| 113 | PRE | 1.00 | 40 | 100 | 40 | 0 | 20 | 0 | 0 | 0 |
| | POST | 1.00 | 0 | 80 | 50 | 20 | 35 | 20 | 0 | 10 |
| 114 | PRE | 1.00 | 0 | 80 | 20 | 0 | 50 | 95 | 60 | 50 |
| | POST | 1.00 | 0 | 80 | 40 | 20 | 40 | 30 | 0 | 0 |
| 115 | PRE | 1.00 | 100 | 100 | 25 | 0 | 40 | 100 | 60 | 90 |
| | POST | 1.00 | 0 | 80 | 60 | 20 | 0 | 50 | 0 | 0 |
| 116 | PRE | 1.00 | 50 | 100 | 100 | 60 | 100 | 100 | 100 | 100 |
| | POST | 1.00 | 25 | 95 | 100 | 85 | 90 | 95 | 80 | 95 |
| 117 | PRE | 1.00 | 80 | 100 | 40 | 35 | 95 | 95 | 100 | 95 |
| | POST | 1.00 | 20 | 90 | 25 | 35 | 50 | 60 | 30 | 25 |
| 118 | PRE | 1.00 | 50 | 95 | 80 | 0 | 95 | 100 | 95 | 95 |
| | POST | 1.00 | 60 | 90 | 95 | 40 | 90 | 95 | 85 | 90 |
| 119 | PRE | 1.00 | 85 | 95 | 80 | 0 | 90 | 100 | 100 | 95 |
| | POST | 1.00 | 80 | 90 | 95 | 70 | 90 | 95 | 70 | 75 |
| 120 | PRE | 1.00 | 0 | 0 | 0 | 0 | 25 | 20 | 20 | 0 |
| | POST | 1.00 | 25 | 80 | 60 | 50 | 40 | 40 | 25 | 10 |
| 121 | PRE | 1.00 | 90 | 95 | 40 | 25 | 85 | 95 | 100 | 80 |
| | POST | 1.00 | 25 | 100 | 100 | 75 | 90 | 90 | 80 | 85 |
| 122 | PRE | 1.00 | 80 | 95 | 70 | 60 | 100 | 100 | 100 | 100 |
| | POST | 1.00 | 50 | 90 | 80 | 60 | 85 | 85 | 80 | 60 |
| 123 | PRE | 1.00 | 100 | 100 | 95 | 40 | 100 | 100 | 100 | 100 |
| | POST | 1.00 | 75 | 100 | 100 | 35 | 95 | 90 | 85 | 85 |
| 124 | PRE | 4.00 | 95 | 75 | 0 | 0 | 10 | 90 | 10 | 20 |
| | POST | 4.00 | 25 | 100 | 80 | 50 | 80 | 80 | 25 | 40 |
| 125 | PRE | 1.00 | 95 | 100 | 95 | 40 | 100 | 100 | 100 | 100 |
| | POST | 1.00 | 85 | 100 | 100 | 80 | 95 | 95 | 90 | 90 |
| 126 | PRE | 1.00 | 95 | 95 | 50 | 0 | 100 | 100 | 100 | 100 |
| | POST | 1.00 | 30 | 90 | 80 | 70 | 95 | 95 | 95 | 95 |
| 127 | PRE | 1.00 | 0 | 0 | 0 | 0 | 0 | 0 | 0 | 0 |
| | POST | 1.00 | 0 | 25 | 10 | 0 | 0 | 10 | 0 | 0 |
| 128 | PRE | 1.00 | 0 | 85 | 20 | 0 | 60 | 85 | 95 | 85 |
| | POST | 1.00 | 80 | 80 | 60 | 40 | 10 | 70 | 25 | 10 |
| 129 | PRE | 1.00 | 100 | 100 | 60 | 0 | 100 | 95 | 100 | 100 |
| | POST | 1.00 | 40 | 95 | 85 | 75 | 95 | 90 | 85 | 85 |
| 130 | PRE | 1.00 | 95 | 100 | 100 | 60 | 100 | 100 | 100 | 100 |
| | POST | 1.00 | 35 | 100 | 100 | 95 | 95 | 95 | 90 | 95 |
| 131 | PRE | 1.00 | 0 | 20 | 0 | 0 | 80 | 95 | 60 | 50 |
| | POST | 1.00 | 0 | 80 | 25 | 25 | 20 | 70 | 0 | 0 |
| 132 | PRE | 1.00 | 0 | 100 | 95 | 10 | 100 | 100 | 100 | 100 |
| | POST | 1.00 | 40 | 100 | 100 | 80 | 90 | 95 | 85 | 95 |

"—" MEANS NOT TESTED

TABLE 3B

| COMPOUND | TYPE | g/HA | BID | BYG | CRB | FOX | MF | NS | SMT | VEL |
|---|---|---|---|---|---|---|---|---|---|---|
| 133 | POST | 1200 | 40 | 20 | 70 | 0 | 0 | 80 | 50 | 40 |
| | PRE | 1200 | 20 | 60 | 100 | 40 | 10 | 100 | 20 | 0 |
| 134 | POST | 1200 | 80 | 85 | 95 | 85 | 80 | 90 | 85 | 80 |
| | PRE | 1200 | 100 | 100 | 100 | 100 | 100 | 100 | 100 | 100 |
| 135 | POST | 1200 | 25 | 90 | 100 | 70 | 75 | 90 | 75 | 40 |
| | PRE | 1200 | 95 | 100 | 100 | 100 | 100 | 100 | 100 | 0 |
| 136 | POST | 1200 | 85 | 90 | 100 | 95 | 95 | 95 | 85 | 60 |
| | PRE | 1200 | 95 | 95 | 95 | 95 | 95 | 100 | 95 | 25 |
| 137 | POST | 1200 | 60 | 0 | 85 | 0 | 0 | 80 | 70 | 10 |
| | PRE | 1200 | 25 | 90 | 95 | 95 | 95 | 100 | 75 | 0 |
| 138 | POST | 1200 | 0 | 0 | 0 | 0 | 0 | 25 | 0 | 0 |
| | PRE | 1200 | 70 | 0 | 0 | 0 | 0 | 25 | 0 | 0 |
| 139 | POST | 1200 | 0 | 0 | 0 | 0 | 0 | C | 0 | 0 |
| | PRE | 1200 | 0 | 10 | 75 | 0 | 0 | 85 | 0 | 0 |
| 140 | POST | 1200 | 25 | 90 | 100 | 100 | 95 | 100 | 100 | 80 |
| | PRE | 1200 | 0 | 100 | 100 | 100 | 100 | 100 | 100 | 80 |
| 141 | POST | 1200 | 0 | 0 | 0 | 0 | 0 | 70 | 10 | 0 |
| | PRE | 1200 | 100 | 0 | 100 | 100 | 25 | 100 | 95 | 0 |
| 142 | POST | 1200 | 0 | 0 | 0 | 0 | 0 | 0 | 0 | 0 |
| | PRE | 1200 | 0 | 0 | 60 | 95 | 0 | 0 | 0 | 0 |
| 143 | POST | 1200 | 25 | 85 | 90 | 90 | 90 | 95 | 85 | 75 |
| | PRE | 1200 | 100 | 100 | 100 | 100 | 100 | 100 | 100 | 100 |
| 144 | POST | 1200 | 20 | 85 | 95 | 40 | 80 | 100 | 90 | 10 |
| | PRE | 1200 | 25 | 100 | 100 | 100 | 100 | 100 | 40 | 0 |
| 145 | POST | 1200 | 50 | 100 | 100 | 95 | 95 | 100 | 50 | 40 |
| | PRE | 1200 | 100 | 100 | 100 | 100 | 100 | 100 | 100 | 50 |
| 146 | POST | 1200 | 25 | 95 | 100 | 90 | 95 | 100 | 75 | 20 |
| | PRE | 1200 | 100 | 100 | 100 | 100 | 100 | 100 | 100 | 80 |
| 147 | POST | 1200 | 10 | 100 | 95 | 80 | 95 | 100 | 100 | 40 |
| | PRE | 1200 | 95 | 100 | 100 | 100 | 100 | 100 | 100 | 95 |
| 148 | POST | 1200 | 25 | 90 | 90 | 95 | 95 | 100 | 100 | 80 |

TABLE 3B-continued

| COMPOUND | TYPE | g/HA | BID | BYG | CRB | FOX | MF | NS | SMT | VEL |
|---|---|---|---|---|---|---|---|---|---|---|
| | PRE | 1200 | 100 | 100 | 100 | 100 | 100 | 100 | 100 | 80 |
| 149 | POST | 1200 | 50 | 95 | 95 | 95 | 95 | 100 | 95 | 70 |
| | PRE | 1200 | 100 | 100 | 100 | 100 | 100 | 100 | 100 | 100 |
| 150 | POST | 1200 | 0 | 0 | 20 | 0 | 0 | 20 | 0 | 0 |
| | PRE | 1200 | 0 | 0 | 95 | 50 | 10 | 20 | 0 | 0 |
| 151 | POST | 1200 | 40 | 20 | 10 | 20 | 10 | 70 | 75 | 0 |
| | PRE | 1200 | 95 | 100 | 100 | 95 | 100 | 100 | 80 | 20 |
| 152 | POST | 1200 | 50 | 80 | 85 | 80 | 85 | 100 | 80 | 25 |
| | PRE | 1200 | 0 | 100 | 100 | 100 | 100 | 100 | 100 | 0 |
| 153 | POST | 1200 | 90 | 90 | 85 | 90 | 100 | 95 | 95 | 80 |
| | PRE | 1200 | 100 | 100 | 100 | 100 | 100 | 100 | 100 | 100 |
| 154 | POST | 1200 | 70 | 85 | 95 | 90 | 85 | 100 | 85 | 80 |
| | PRE | 1200 | 100 | 100 | 100 | 100 | 100 | 100 | 100 | 80 |
| 155 | POST | 1200 | 25 | 70 | 90 | 25 | 80 | 100 | 70 | 40 |
| | PRE | 1200 | 0 | 100 | 100 | 100 | 100 | 100 | 100 | 0 |
| 156 | POST | 1200 | 0 | 0 | 40 | 0 | 0 | 60 | 0 | 0 |
| | PRE | 1200 | 0 | 25 | 95 | 100 | 100 | 95 | 25 | 20 |
| 157 | POST | 1200 | 10 | 50 | 85 | 20 | 50 | 95 | 75 | 70 |
| | PRE | 1200 | 0 | 100 | 100 | 100 | 100 | 100 | 75 | 10 |
| 158 | POST | 1200 | 40 | 40 | 90 | 70 | 60 | 90 | 80 | 20 |
| | PRE | 1200 | 80 | 70 | 100 | 100 | 95 | 100 | 100 | 0 |
| 158 | POST | 1200 | 75 | 85 | 90 | 85 | 85 | 95 | 85 | 70 |
| | PRE | 1200 | 0 | 100 | 100 | 100 | 100 | 100 | 100 | 60 |
| 160 | POST | 1200 | 10 | 40 | 90 | 10 | 25 | 95 | 20 | 10 |
| | PRE | 1200 | 70 | 75 | 100 | 100 | 95 | 100 | 80 | 25 |
| 161 | POST | 1200 | 10 | 90 | 95 | 90 | 95 | 100 | 90 | 30 |
| | PRE | 1200 | 0 | 100 | 95 | 100 | 100 | 100 | 100 | 20 |
| 162 | POST | 1200 | 10 | 10 | 75 | 10 | 0 | 75 | 10 | 10 |
| | PRE | 1200 | 40 | 0 | 100 | 0 | 20 | 40 | 20 | 0 |
| 163 | POST | 1200 | 40 | 90 | 90 | 70 | 95 | 95 | 75 | 35 |
| | PRE | 1200 | 0 | 100 | 100 | 100 | 100 | 100 | 70 | 0 |
| 164 | POST | 1200 | 20 | 95 | 95 | 40 | 90 | 80 | 70 | 20 |
| | PRE | 1200 | 95 | 100 | 100 | 100 | 100 | 100 | 100 | 25 |
| 165 | POST | 1200 | 20 | 10 | 10 | 10 | 10 | 75 | 10 | 10 |
| | PRE | 1200 | 90 | 25 | 95 | 0 | 0 | 100 | 0 | 0 |
| 166 | POST | 1200 | 20 | 95 | 95 | 100 | 100 | 100 | 90 | 60 |
| | PRE | 1200 | 0 | 100 | 100 | 100 | 100 | 100 | 100 | 100 |
| 167 | POST | 1200 | 0 | 10 | 95 | 10 | 10 | 85 | 25 | 0 |
| | PRE | 1200 | 0 | 40 | 95 | 20 | 10 | 95 | 0 | 0 |
| 168 | POST | 1200 | 85 | 80 | 90 | 80 | 90 | 70 | 70 | 40 |
| | PRE | 1200 | 25 | 95 | 95 | 100 | 100 | 100 | 25 | 25 |
| 169 | POST | 1200 | 0 | 0 | 50 | 0 | 0 | 80 | 0 | 0 |
| | PRE | 1200 | 0 | 90 | 95 | 95 | 10 | 100 | 0 | 0 |
| 170 | POST | 1200 | 0 | 20 | 95 | 0 | 25 | 95 | 50 | 10 |
| | PRE | 1200 | 0 | 90 | 100 | 95 | 90 | 95 | 40 | 0 |
| 171 | POST | 1200 | 10 | 40 | 90 | 40 | 60 | 90 | 70 | 0 |
| | PRE | 1200 | 0 | 90 | 95 | 100 | 95 | 95 | 50 | 0 |
| 172 | POST | 1200 | 25 | 80 | 95 | 90 | 90 | 10 | 95 | 10 |
| | PRE | 1200 | 100 | 100 | 95 | 100 | 100 | 100 | 100 | 10 |
| 173 | POST | 1200 | 25 | 25 | 25 | 20 | 20 | 90 | 20 | 20 |
| | PRE | 1200 | 100 | 100 | 95 | 100 | 100 | 100 | 100 | 40 |
| 174 | POST | 1200 | 0 | 0 | 0 | 0 | 0 | 80 | 10 | 0 |
| | PRE | 1200 | 20 | 70 | 40 | 80 | 70 | 40 | 20 | 10 |
| 175 | POST | 1200 | 0 | 0 | 0 | 0 | 0 | 95 | 10 | 10 |
| | PRE | 1200 | 95 | 95 | 100 | 95 | 100 | 100 | 70 | 20 |
| 176 | POST | 1200 | 90 | 80 | 80 | 70 | 85 | 90 | 90 | 85 |
| | PRE | 1200 | 0 | 100 | 95 | 100 | 95 | 80 | 80 | 80 |
| 177 | POST | 1200 | 0 | 70 | 75 | 0 | 0 | 95 | 60 | 0 |
| | PRE | 1200 | 40 | 100 | 100 | — | 100 | 100 | 90 | 10 |
| 178 | POST | 1200 | 0 | 65 | 75 | 20 | 40 | 95 | 60 | 25 |
| | PRE | 1200 | 20 | 95 | 95 | — | 100 | 100 | 75 | 25 |
| 179 | POST | 1200 | 0 | 20 | 70 | 0 | 20 | 70 | 10 | 0 |
| | PRE | 1200 | 0 | 70 | 100 | — | 100 | 90 | 60 | 20 |
| 180 | POST | 1200 | 80 | 75 | 60 | 65 | 90 | 90 | 75 | 40 |
| | PRE | 1200 | 100 | 100 | 100 | — | 100 | 100 | 100 | 75 |
| 181 | POST | 1200 | 0 | 0 | 0 | 0 | 0 | 10 | 0 | 0 |
| | PRE | 1200 | 100 | 25 | 100 | — | 25 | 70 | 100 | 100 |
| 182 | POST | 1200 | 0 | 80 | 95 | 10 | 0 | 90 | 90 | 10 |
| | PRE | 1200 | 0 | 100 | 100 | — | 100 | 95 | 95 | 95 |
| 183 | POST | 1200 | 40 | 75 | 85 | 70 | 75 | 95 | 80 | 40 |
| | PRE | 1200 | 95 | 95 | 100 | 95 | 95 | 95 | 95 | 60 |
| 184 | POST | 1200 | 20 | 90 | 65 | 75 | 25 | 95 | 85 | 75 |
| | PRE | 1200 | 100 | 95 | 95 | 95 | 95 | 95 | 100 | 40 |
| 185 | POST | 4800 | 10 | 0 | 0 | 0 | 0 | 40 | 20 | 75 |
| | PRE | 4800 | 0 | 100 | 100 | 100 | 100 | 75 | 20 | 0 |

It is to be understood that changes and variations may be made without departing from the spirit and scope of the invention as defined by the appended claims.

What is claimed is:

1. A compound of the formula:

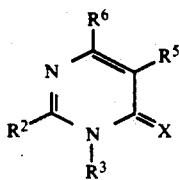

wherein
(a) $R^2$ is a furyl, phenyl, naphthyl, pyridyl, or thienyl group,
each of said group is optionally substituted with up to three substituents independently selected from a bromo, chloro, fluoro, $(C_1-C_{12})$alkyl, cyclo$(C_3-C_8)$alkyl, $(C_2-C_{12})$alkenyl, cyclo$(C_3-C_8)$alkenyl, $(C_2-C_{12})$alkynyl, halo$(C_1-C_{12})$alkyl, polyhalo$(C_1-C_{12})$alkyl, halo$(C_2-C_{12})$alkenyl, polyhalo$(C_2-C_{12})$alkenyl, halo$(C_2-C_6)$alkynyl, polyhalo$(C_2-C_6)$alkynyl, $(C_1-C_{12})$alkoxy, $(C_1-C_{12})$alkylthio, $(C_1-C_{12})$alkylsulfonyl, $(C_1-C_{12})$alkylsulfinyl, phenyl, phen$(C_1-C_{12})$alkyl, phen$(C_2-C_{12})$alkenyl, phen$(C_2-C_{12})$alkynyl, cyano, halo$(C_1-C_{12})$alkoxy, 1,3-dioxalan-2-yl, hydroxyimino, or nitro group; and when $R^2$ is pyridyl, such pyridyl group is optionally substituted with oxygen on the nitrogen of the pyridyl group; or $R^2$ is a furyl, phenyl, naphthyl, pyridyl or thienyl group having a fused ring moiety composed of an oxymethyleneoxy or an oxoethyleneoxy link bonds to adjacent carbon atoms or said group;

(b) $R^3$ is a $(C_1-C_3)$alkyl, halo$(C_1-C_3)$alkyl, polyhalo$(C_1-C_3)$alkyl, $(C_3-C_4)$alkenyl, $(C_5-C_6)$alkenynyl, $(C_3-C_6)$alkynyl, $(C_1-C_6)$alkoxy$(C_1-C_6)$alkyl, di$(C_1-C_6)$alkoxy$(C_1-C_6)$alkyl, halo$(C_1-C_6)$alkoxy$(C_1-C_6)$alkyl, or 2-oxo$(C_2-C_3)$alkyl, trimethylsilyl$(C_3-C_4)$alkynyl or cyano$(C_1-C_6)$alkyl group, each of said $(C_3-C_4)$alkenyl, or $(C_3-C_6)$alkynyl group is optionally substituted with up to five halogens; and (c) $R^5$ is a hydrogen, $(C_1-C_5)$alkyl, $(C_3-C_6)$alkenyl, $(C_2-C_6)$alkynyl, halo$(C_1-C_6)$alkyl, polyhalo$(C_1-C_6)$alkyl, halo$(C_2-C_6)$alkenyl, polyhalo$(C_2-C_6)$alkenyl, halo$(C_2-C_6)$alkynyl, polyhalo$(C_2-C_6)$alkynyl, halo$(C_1-C_6)$alkoxy, polyhalo$(C_1-C_6)$alkoxy, trimethylsilyl$(C_2-C_3)$alkynyl, $(C_1-C_6)$alkoxy, $(C_1-C_6)$alkylthio, $(C_1-C_3)$alkoxycarbonyl$(C_1-C_3)$alkyl, halo, or cyano group; and (d) $R^6$ is a hydrogen, halo, $(C_1-C_8)$alkyl, $(C_2-C_6)$alkenyl, $(C_2-C_6)$alkynyl, halo$(C_1-C_6)$alkyl, polyhalo$(C_1-C_6)$alkyl, halo$(C_2-C_6)$alkenyl, polyhalo$(C_2-C_6)$alkenyl, halo$(C_2-C_6)$alkynyl, polyhalo$(C_2-C_6)$alkynyl, $(C_1-C_6)$alkoxy, $(C_1-C_6)$alkoxy$(C_1-C_4)$alkyl, $(C_1-C_6)$alkylthio, $(C_1-C_3)$alkoxycarbonyl, $(C_1-C_3)$alkoxycarbonyl$(C_1-C_3)$alkyl, $(C_6-C_{10})$aryl, ar$(C_1-C_4)$alkyl, cyclo$(C_3-C_7)$alkyl, $(C_4-C_5)$heterocyclyl selected from a group consisting of furyl, pyridyl and thienyl, $(C_1-C_3)$alkylamino, di$(C_1-C_3)$alkylamino, di$(C_1-C_3)$alkylaminocarbonyl, halo$(C_1-C_6)$alkylthio, polyhalo$(C_1-C_6)$alkythio, halo$(C_1-C_6)$alkoxy, polyhalo$(C_1-C_6)$alkoxy, $(C_6-C_{10})$aryloxy or cyano group; said $(C_6-C_{10})$aryl, ar$(C_1-C_4)$alkyl and $(C_6-C_{10})$aryloxy groups being optionally substituted with up to three substituents independently selected from bromo; chloro; fluoro; $(C_1-C_{12})$alkyl, cyclo$(C_3-C_8)$alkyl, $(C_2-C_{12})$alkenyl, cyclo$(C_3-C_8)$alkenyl, $(C_2-C_{12})$alkynyl, halo$(C_1-C_{12})$alkyl, polyhalo$(C_1-C_{12})$alkyl, halo$(C_2-C_{12})$alkenyl, polyhalo$(C_2-C_{12})$alkenyl, halo$(C_2-C_6)$alkynyl, polyhalo$(C_2-C_6)$alkynyl; $(C_1-C_{12})$alkoxy, $(C_1-C_{12})$alkylthio, $(C_1-C_{12})$alkylsulfonyl, $(C_1-C_{12})$alkylsulfinyl, phenyl, phen$(C_1-C_{12})$alkyl, phen$(C_2-C_{12})$alkenyl, phen$(C_2-C_{12})$alkynyl, cyano, halo$(C_1-C_{12})$alkoxy, 1,3-dioxalan-2-yl, hydroxyimino, and nitro; and (e) X is oxygen or sulfur;
provided that
(1) when $R^2$ and $R^6$ are phenyl, then $R^5$ is neither alkyl nor cyano;
(2) when $R^2$ is phenyl, then $R^6$ is neither alkyl nor haloalkyl; and
(3) when X is sulfur and $R^2$ is phenyl, then $R^3$ is not alkyl.

2. The compound of claim 1 wherein $R^2$ is
(a) a phenyl, 3-methylphenyl, 3-methoxyphenyl, 3-nitrophenyl, 4-fluorophenyl, 4-chlorophenyl, 3-trifluoromethylphenyl, 3-bromophenyl, 3-chlorophenyl, 3-fluorophenyl, 3-trifluoromethoxyphenyl, 3-cyanophenyl, 3-(1,3-dioxolan-2-yl)-phenyl, 3-(hydroxyimino)phenyl, 2-fluorophenyl, 2-chlorophenyl, 2-trifluoromethoxyphenyl, 3,5-difluorophenyl, 3,5-dichlorophenyl, 2,4-difluorophenyl, 2,5-difluorophenyl, 3-chloro-4-fluorophenyl, 3,4-difluorophenyl, 3-fluoro-5-trifluoromethylphenyl, or 3,4,5-trifluorophenyl group; or
(b) a 6-chloro-2-pyridyl, 3-pyridyl, 1-methyl-3-pyridinium halide, 5-bromo-3-pyridyl, 5,6-dichloro-3-pyridyl, 5-chloro-3-pyridyl, 1-oxo-3-pyridyl, 4-pyridyl, 2-fluoro-4-pyridyl, 2-methyl-4-pyridyl, 2-methoxy-4-pyridyl, 2-cyano-4-pyridyl, 1-oxo-4-pyridyl, 2-chloro-4-pyridyl, 2-chloro-6-methyl-4-pyridyl, 2,6-difluoro-4-pyridyl or 2,6-dichloro-4-pyridyl group; or
(c) a 2-furyl or 3-furyl group; or
(d) a 2-thienyl, 3-thienyl, 4-chloro-2-thienyl, 5-chloro-2-thienyl, 5-chloro-3-thienyl, or 2,5-dichloro-3-thienyl group.

3. The compound of claim 1 wherein $R^3$ is an allyl, pent-2-ynyl, prop-2-ynyl, but-2-ynyl, methoxymethyl, 2-methoxyethyl, acetonyl, 2,2-dimethoxypropyl, pent-4-en-2-ynyl, 3-chloroallyl, 3-iodopropargyl, 3-trimethylsilyl propargyl, or cyanomethyl group.

4. The compound of claim 1 wherein $R^5$ is a hydrogen, fluoro, chloro, methyl, ethyl, n-propyl, i-propyl, prop-2-ynyl, trimethylsilylethynyl, methylthio, methoxy, methoxycarbonylmethyl, allyl, fluoromethyl, or trifluoromethyl group.

5. The compound of claim 1 wherein $R^6$ is
(a) a methyl, ethyl, n-propyl, n-butyl, n-pentyl, n-hexyl, n-heptyl, i-propyl, i-butyl, s-butyl, or t-butyl group; or
(b) a 2-methyl-1-propenyl group; or
(c) a substituted or unsubstituted phenyl group; or
(d) a 3-thienyl, 3-furyl, 2-thienyl or 4-pyridyl group; or
(e) a methoxy or ethoxy group; or
(f) an ethoxycarbonyl group; or
(g) a fluoro, bromo, or chloro group; or
(h) a trifluoromethyl, difluoromethyl, pentafluoroethyl, trichloromethyl, bromomethyl, chloromethyl, or chlorodifluoromethyl group; or
(i) a methylthio group; or
(j) a methoxymethyl group; or
(k) a benzyl group; or (l) a cyclopropyl, cyclobutyl or cyclopentyl group; or (m) a dimethylamino group; or (n) a dimethylaminocarbonyl group; or (o) hydrogen.

6. The compound of claim 1 wherein X is oxygen.

7. The compound of claim 1 wherein $R^5$ is selected from hydrogen, halo, $(C_1-C_4)$alkyl, polyhalo$(C_1-C_4)$alkyl, and $(C_1-C_4)$alkoxy; and $R^6$ is selected from hydrogen, halo, $(C_1-C_4)$alkyl, unsubstituted phenyl, substituted phenyl, polyhalo$(C_1-C_4)$alkyl, and $(C_1-C_4)$alkoxy.

8. The compound of claim 7 wherein

X is oxygen;

$R^2$ is phenyl, 3-substituted phenyl or 3,5-disubstituted-phenyl or 3,4,5-trisubstituted-phenyl or 2-substituted-4-pyridyl or 2,6-disubstituted-4-pyridyl or 3-thienyl or 5-substituted-3-thienyl;

$R^3$ is $(C_3-C_6)$alkynyl;

$R^5$ is selected from hydrogen, halo, $(C_1-C_4)$alkyl, polyhalo$(C_1-C_4)$alkyl and $(C_1-C_4)$alkoxy; and $R^6$ is selected from hydrogen, halo, $(C_1-C_4)$alkyl, unsubstituted phenyl, substituted phenyl, polyhalo$(C_1-C_4)$alkyl and $(C_1-C_4)$alkoxy.

9. The compound of claim 8 wherein

X is oxygen;

$R^2$ is phenyl, 3-fluorophenyl, 3-chlorophenyl, 3,5-difluorophenyl, 3,4,5-trifluorophenyl, 3,5-dichlorophenyl, 2-chloro-4-pyridyl, 2-fluoro-4-pyridyl, or 2,6-dichloro-4-pyridyl, 3-thienyl or 5-chloro-3-thienyl;

$R^3$ is propargyl;

$R^5$ is hydrogen, methyl, ethyl, methoxy, fluoro or chloro; and $R^6$ is hydrogen, methyl, ethyl, isopropyl, n-propyl, n-butyl, s-butyl, i-butyl, t-butyl, difluoromethyl, trifluoromethyl, phenyl, chloro, bromo, or fluoro.

10. The compound of claim 9 selected from (a) 5,6-diethyl-2-phenyl-3-propargyl-4(3H)-pyrimidinone;

(b) 5-ethyl-2-phenyl-3-propargyl-6-trifluoromethyl-4(3H)-pyrimidinone;

(c) 5-ethyl-6-isopropyl-2-phenyl-3-propargyl-4(3H)-pyrimidinone;

(d) 6-chloro-5-ethyl-2-phenyl-3-propargyl-4(3H)-pyrimidinone;

(e) 5,6-diethyl-2-(3-fluorophenyl)-3-propargyl-4(3H)-pyrimidinone;

(f) 2-(2,6-dichloro-4-pyridyl)-5,6-diethyl-3-propargyl-4(3H)-pyrimidinone;

(g) 5,6-diethyl-2-(3,5-difluorophenyl)-3-propargyl-4(3H)-pyrimidinone;

(h) 5-ethyl-2-phenyl-3-propargyl-6-(n-propyl)-4(3H)-pyrimidinone;

(i) 6-difluoromethyl-5-ethyl-2-phenyl-3-propargyl-4(3H)-pyrimidinone; and (j) 6-ethyl-5-methoxy-2-phenyl-3-propargyl-4(3H)-pyrimidinone.

11. A compound of the formula:

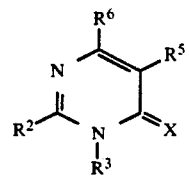

wherein (a) $R^2$ is a phenyl, pyridyl, or thienyl group, each of said group is optionally substituted with up to three substituents independently selected from a bromo, chloro, fluoro, $(C_1-C_{12})$alkyl, cyclo$(C_3-C_8)$alkyl, $(C_2-C_{12})$alkenyl, cyclo$(C_3-C_8)$alkenyl, $(C_2-C_{12})$alkynyl, halo$(C_1-C_{12})$alkyl, polyhalo$(C_1-C_{12})$alkyl, halo$(C_2-C_{12})$alkenyl, polyhalo$(C_2-C_{12})$alkenyl, halo$(C_2-C_6)$alkynyl, polyhalo$(C_2-C_6)$alkynyl, $(C_1-C_{12})$alkoxy, $(C_1-C_{12})$alkylthio, $(C_1-C_{12})$alkylsulfonyl, $(C_1-C_{12})$alkylsulfinyl, phenyl, phen$(C_1-C_{12})$alkyl, phen$(C_2-C_{12})$alkenyl, phen$(C_2-C_{12})$alkynyl, cyano, halo$(C_1-C_{12})$alkoxy, 1,3-dioxolan-2-yl, hydroxyimino, or nitro group; and when $R^2$ is pyridyl, such pyridyl group is optionally substituted with oxygen on the nitrogen of the pyridyl group;

(b) $R^3$ is a $(C_3-C_6)$alkynyl group optionally substituted with up to five halogens; and (c) $R^5$ is a hydrogen, $(C_1-C_5)$alkyl, $(C_3-C_6)$alkenyl, $(C_2-C_6)$alkynyl, halo$(C_1-C_6)$alkyl, polyhalo$(C_1-C_6)$alkyl, halo$(C_2-C_6)$alkenyl, polyhalo$(C_2-C_6)$alkenyl, halo$(C_2-C_6)$alkynyl, polyhalo$(C_2-C_6)$alkynyl, halo$(C_1-C_6)$alkoxy, polyhalo$(C_1-C_6)$alkoxy, trimethylsilyl$(C_2-C_3)$alkynyl, $(C_1-C_6)$alkoxy, $(C_1-C_6)$alkylthio, $(C_1-C_3)$alkoxycarbonyl$(C_1-C_3)$alkyl, halo, or cyano group; and (d) $R^6$ is a hydrogen, halo, $(C_1-C_8)$alkyl, $(C_2-C_6)$alkenyl, $(C_2-C_6)$alkynyl, halo$(C_1-C_6)$alkyl, polyhalo$(C_1-C_6)$alkyl, halo$(C_2-C_6)$alkenyl, polyhalo$(C_2-C_6)$alkenyl, halo$(C_2-C_6)$alkynyl, polyhalo$(C_2-C_6)$alkynyl, $(C_1-C_6)$alkoxy, $(C_1-C_6)$alkoxy$(C_1-C_4)$alkyl, $(C_1-C_6)$alkylthio, $(C_1-C_3)$alkoxycarbonyl, $(C_1-C_3)$alkoxycarbonyl$(C_1-C_3)$alkyl, $(C_6-C_{10})$aryl, ar$(C_1-C_4)$alkyl, cyclo$(C_3-C_7)$alkyl, $(C_4-C_5)$heterocyclyl selected from a group consisting of furyl, pyridyl and thienyl, $(C_1-C_3)$alkylamino, di$(C_1-C_3)$alkylamino, di$(C_1-C_3)$alkylaminocarbonyl, halo$(C_1-C_6)$alkylthio, polyhalo$(C_1-C_6)$alkythio, halo$(C_1-C_6)$alkoxy, polyhalo$(C_1-C_6)$alkoxy, $(C_6-C_{10})$aryloxy or cyano group; said $(C_6-C_{10})$aryl, ar$(C_1-C_4)$alkyl and $(C_6-C_{10})$aryloxy groups being optionally substituted with up to three substituents independently selected from bromo; chloro; fluoro; $(C_1-C_{12})$alkyl, cyclo$(C_3-C_8)$alkyl, $(C_2-C_{12})$alkenyl, cyclo$(C_3-C_8)$alkenyl, $(C_2-C_{12})$alkynyl, halo$(C_1-C_{12})$alkyl, polyhalo$(C_1-C_{12})$alkyl, halo$(C_2-C_{12})$alkenyl, polyhalo$(C_2-C_{12})$alkenyl, halo$(C_2-C_6)$alkynyl, polyhalo$(C_2-C_6)$alkynyl; $(C_1-C_{12})$alkoxy, $(C_1-C_{12})$alkylthio, $(C_1-C_{12})$alkylsulfonyl, $(C_1-C_{12})$alkylsulfinyl, phenyl, phen$(C_1-C_{12})$alkyl, phen$(C_2-C_{12})$alkenyl, phen$(C_2-C_{12})$alkynyl, cyano, halo$(C_1-C_{12})$alkoxy, 1,3-dioxalan-2-yl, hydroxyimino, and nitro; and (e) X is oxygen or sulfur.

12. A herbicidal composition comprising a herbicidally effective amount of a compound of the formula:

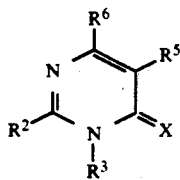

wherein (a) $R^2$ is a furyl, phenyl, naphthyl, pyridyl, or thienyl group, each of said group is optionally substituted with up to three substituents independently selected from a bromo, chloro, fluoro, $(C_1-C_{12})$alkyl, cyclo$(C_3-C_8)$alkyl, $(C_2-C_{12})$alkenyl, cyclo$(C_3-C_8)$alkenyl, $(C_2-C_{12})$alkynyl, halo$(C_1-C_{12})$alkyl, polyhalo$(C_1-C_{12})$alkyl, halo$(C_2-C_{12})$alkenyl, polyhalo$(C_2-C_{12})$alkenyl, halo$(C_2-C_6)$alkynyl, polyhalo$(C_2-C_6)$alkynyl, $(C_1-C_{12})$alkoxy, $(C_1-C_{12})$alkylthio, $(C_1-C_{12})$alkylsulfonyl, $(C_1-C_{12})$alkylsulfinyl, phenyl, phen$(C_1-C_{12})$alkyl, phen$(C_2-C_{12})$alkenyl, phen$(C_2-C_{12})$alkynyl, cyano, halo$(C_1-C_{12})$alkoxy, 1,3-dioxolan-2-yl, hydroxyimino, or nitro group; and when $R^2$ is pyridyl, such pyridyl group is optionally substituted with oxygen on the nitrogen of the pyridyl group; or $R^2$ is a furyl, phenyl, naphthyl, pyridyl or thienyl group having a fused ring moiety composed of an oxymethyleneoxy or an oxoethyleneoxy link bonds to adjacent carbon atoms or said group;

(b) $R^3$ is a $(C_1-C_3)$alkyl, $(C_3-C_4)$alkenyl, $(C_5-C_6)$alkenynyl, $(C_3-C_6)$alkynyl, $(C_1-C_6)$alkoxy$(C_1-C_6)$alkyl, di$(C_1-C_6)$alkoxy$(C_1-C_6)$alkyl, (halo$(C_1-C_6)$alkoxy$(C_1-C_6)$alkyl, 2-oxo$(C_2-C_3)$alkyl, trimethylsilyl$(C_3-C_4)$alkynyl, cyano$(C_1-C_6)$alkyl, or phenyl group, each of said $(C_1-C_3)$alkyl, $(C_3-C_4)$alkenyl, or $(C_3-C_6)$alkynyl group is optionally substituted with up to five halogens; and (c) $R^5$ is a hydrogen, $(C_1-C_5)$alkyl, $(C_3-C_6)$alkenyl, $(C_2-C_6)$alkynyl, halo$(C_1-C_6)$alkyl, polyhalo$(C_1-C_6)$alkyl, halo$(C_2-C_6)$alkenyl, polyhalo$(C_2-C_6)$alkenyl, halo$(C_2-C_6)$alkynyl, polyhalo$(C_2-C_6)$alkynyl, trimethylsilyl$(C_2-C_3)$alkynyl, $(C_1-C_6)$alkoxy, halo$(C_1-C_6)$alkoxy, polyhalo$(C_1-C_6)$alkoxy, $(C_1-C_6)$alkylthio, $(C_1-C_3)$alkoxycarbonyl$(C_1-C_3)$alkyl, halo, or cyano group; and (d) $R^6$ is a hydrogen, halo $(C_1-C_8)$alkyl, $(C_2-C_6)$alkenyl, $(C_2-C_6)$alkynyl, halo$(C_1-C_6)$alkyl, polyhalo$(C_1-C_6)$alkyl, halo$(C_2-C_6)$alkenyl, polyhalo$(C_2-C_6)$alkenyl, halo$(C_2-C_6)$alkynyl, polyhalo$(C_2-C_6)$alkynyl, $(C_1-C_6)$alkoxy, $(C_1-C_4)$alkyl, $(C_1-C_6)$alkylthio, $(C_1-C_3)$alkoxycarbonyl, $(C_1-C_3)$alkoxycarbonyl$(C_1-C_3)$alkyl, $(C_6-C_{10})$aryl, ar$(C_1-C_4)$alkyl, cyclo$(C_3-C_7)$alkyl, $(C_4-C_5)$heterocyclyl selected from a group consisting of furyl, thienyl or pyridyl, $(C_1-C_3)$alkylamino, di$(C_1-C_3)$alkylamino, di$(C_1-C_3)$alkylaminocarbonyl, halo$(C_1-C_6)$alkylthio, polyhalo$(C_1-C_6)$alkythio, halo$(C_1-C_6)$alkoxy, polyhalo$(C_1-C_6)$alkoxy, $(C_6-C_{10})$aryloxy or cyano group; said $(C_6-C_{10})$aryl, ar$(C_1-C_4)$alkyl and $(C_6-C_{10})$aryloxy groups being optionally substituted with up to three substituents independently selected from bromo; chloro; fluoro; $(C_1-C_{12})$alkyl, cyclo$(C_3-C_8)$alkyl, $(C_2-C_{12})$alkenyl, cyclo$(C_3-C_8)$alkenyl, $(C_2-C_{12})$alkynyl, halo$(C_1-C_{12})$alkyl, polyhalo$(C_1-C_{12})$alkyl, halo$(C_2-C_{12})$alkenyl, polyhalo$(C_2-C_{12})$alkenyl, halo$(C_2-C_6)$alkynyl, polyhalo$(C_2-C_6)$alkynyl; $(C_1-C_{12})$alkoxy, $(C_1-C_{12})$alkylthio, $(C_1-C_{12})$alkylsulfonyl, $(C_1-C_{12})$alkylsulfinyl, phenyl, phen$(C_1-C_{12})$alkyl, phen$(C_2-C_{12})$alkenyl, phen$(C_2-C_{12})$alkynyl, cyano, halo$(C_1-C_{12})$alkoxy, 1,3-dioxalan-2-yl, hydroxyimino, and nitro; and (e) X is oxygen or sulfur.

13. A method of controlling a weed comprising applying a herbicidally effective amount of a composition of claim 12 to said weed or to the locus of said weed or to the growth medium of said weed.

* * * * *

UNITED STATES PATENT AND TRADEMARK OFFICE
CERTIFICATE OF CORRECTION

PATENT NO. : 5,300,477
DATED : April 5, 1994
INVENTOR(S) : Colin M. Tice

It is certified that error appears in the above-indentified patent and that said Letters Patent is hereby corrected as shown below:

In columns 9 and 10, the following footnotes for Table 1 should be added at the conclusion of Table 1.

--*Mixture with differing $R^6$ substitutents.
**X=S (sulfur).--.

Signed and Sealed this

Seventh Day of March, 1995

Attest:

BRUCE LEHMAN

Attesting Officer

Commissioner of Patents and Trademarks